(12) United States Patent
Oeltgen et al.

(10) Patent No.: US 7,705,119 B1
(45) Date of Patent: Apr. 27, 2010

(54) COMPOSITIONS AND METHODS USEFUL FOR TREATING CIRCULATORY AND HYPOVOLEMIC SHOCK

(75) Inventors: Peter R. Oeltgen, Frankfort, KY (US); Meera Govindaswami, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 11/759,013

(22) Filed: Jun. 6, 2007

Related U.S. Application Data

(60) Provisional application No. 60/910,774, filed on Apr. 9, 2007.

(51) Int. Cl.
*C07K 7/06* (2006.01)
*A61K 38/08* (2006.01)
*A61P 7/08* (2006.01)
*C07H 21/04* (2006.01)

(52) U.S. Cl. ........................ 530/328; 514/15; 514/921; 536/23.1; 930/21

(58) Field of Classification Search ...................... None
See application file for complete search history.

(56) References Cited

U.S. PATENT DOCUMENTS

| | | | |
|---|---|---|---|
| 4,684,624 A | 8/1987 | Hosobuchi et al. |
| 5,618,785 A | 4/1997 | Heavner et al. |
| 6,103,722 A | 8/2000 | Schultz et al. |
| 6,177,407 B1 | 1/2001 | Rodgers et al. |
| 6,294,519 B1 | 9/2001 | Oeltgen et al. |
| 6,316,411 B1 | 11/2001 | Oeltgen et al. |
| 6,380,164 B1 | 4/2002 | Oeltgen et al. |
| 6,544,950 B1 | 4/2003 | Oeltgen et al. |
| 6,645,938 B2 | 11/2003 | Oeltgen et al. |
| 6,875,742 B2 | 4/2005 | Oeltgen et al. |
| 6,900,178 B2 | 5/2005 | Oeltgen et al. |
| 6,967,192 B2 | 11/2005 | Oeltgen et al. |
| 7,060,792 B2 | 6/2006 | Oeltgen et al. |

FOREIGN PATENT DOCUMENTS

WO  WO9956766  11/1999

OTHER PUBLICATIONS

Uebel et al, 1997. Proc Natl Acad Sci USA. 94: 8976-8981.*

Bolling, S.F., Schwartz, C.F., Oeltgen, P.R., Kilgore, K., Su, T-P Opiods confer myocardial toleranct to ischemia: Interaction of delta opioids agonists and antagonists. J Thorac Caradiovasc Surg. 122: 476-81, 2001.

Chien, S., Oeltgen, P.R., Diana, J.M., Salley, R., Su, T-P. Extension of tissue survival time in multiogran block preparation using delta opioid DADLE. J. Thorac Cardiovasc Surg, 107: 964-67, 1994.

Fryer, R.M., Hsu, A., Eels, J.T., Nagase, H., Gross, G.J. Opioid-Induce Second Window of Cardioprotection- potential role of mitochondrial KATP channels, Circ Res. 84: 846-51, 1999.

Fryer, R.M., Wang, Y., Hsu, A.K., Gross, G.J. Essential activation of PKC-δ in opioid-induced cardioprotection. Am J Physiol Heart Cir Physiol. 280:H1346-53, 2001.

Govindaswami, M., Bishop, P.D., Kindy, M.S., Oeltgen, P.R.: Neuroprotective effects of opioid-like hibernation factors in cerebral ischemia. FASEB J 17(5) A895, No. 579.10 (2003).

Govindaswami, M., Rodgers, J.R., Lesnaw, J., Oeltgen, P.R. A cell culture assay for delta opioids and opioid-like hibernation specific factors (HSF). FASEB J. 16:(5)A852, No. 643.25, 2003.

Govindaswami, M., Sanchez, A., Bishop, P.D., Bruce, D.S., Oeltgen, P.R. Opioid-like hibernation factors provide protection to ischemic myocardium. In Heldmaier G, Kingenspor M (eds: Life in the Cold: 11th International Symposium. Berlin, Germany: Springer-Verlag Publishers, pp. 377-384, 2000.

Husted, T.L., Lentch, A.B., Govindaswami, M., Oeltgen, P.R., Rudich, S.M. A delta-2 opioid agonist inhibits p38 MAPK and suppresses activation of murine macrophages. J. Surg Research 28:45-49, 2005.

Karck, M., Tanaka, S., Bolling, S.F., Su, T-P, Oeltgen, P.R., Haverich, A. Myocardial protection by ischemic preconditioning and δ opioid receptor activation in the isolated working rat heart: J Thorac Cardiovasc. Surg. 122: 986-92, 2001.

Kevelaitis, E., Peynet, J., Mousa, C., Launay, J.M., Menaschep. Opening of potassium channels: the common cardioprotective link between preconditioning and natural hibernation? Circ. 99:3079-85, 1999.

Liang, B.T., Gross. G.J. Direct preconditioning of cardiac myocytes via opioid receptors and KATP channels: Circ Res. 84: 1396-00, 1999.

(Continued)

*Primary Examiner*—Bridget E Bunner
*Assistant Examiner*—Zachary C Howard
(74) *Attorney, Agent, or Firm*—Stites & Harbison PLLC; Mandy Wilson Decker

(57) ABSTRACT

Polypeptides, compositions, and methods for treating shock are described. A isolated polypeptide, Deltorphin-E, can be administered without concomitant fluid resuscitation, before, concurrently with, or after the onset of shock or the occurrence of an event that creates a risk of shock. Deltorphin-E can be administered in accordance with the method as part of a preconditioning strategy, which reduces the extent of ischemic injury. Deltorphin-E can be used in preparation for planned ischemia or in a prophylactic manner in anticipation of further ischemic events.

23 Claims, 10 Drawing Sheets

OTHER PUBLICATIONS

Mayfield, K.P., D'Alecy, L.G. Delta-1 opioid agonist acutely increases hypoxic tolerance. J Pharmacol Exp Ther. 268: 683-88 (1994).

McBride, S M., Smith-Sonneborn, J., Oeltgen, P., and Flynn, F.W. Delta2 opioid receptor agonist facilitates mean arterial pressure recovery after hemorrhage in conscious rats. Shock 23(3) 264-268, 2005.

Oeltgen P.R., Govindaswami M., Witzke D.B. 24-hour pretreatment with delta opioid enhances survival from hemorrhagic shock. Acad Emerg Med. 13(2):127-33, 2006.

Oeltgen, P.R., Nilekani, S., Nuchols, P., Spurrier, W.A., Su T-P. Further studies on opioids and hibernation: Delta opioid receptor ligand selectively induced hibernation in summer-active ground squirrels. Life Sciences 43:1565-74, 1988.

Patel, H.H., Hsu, A.K., Peart, J.N., Gross, G.J. Sarcolemmal KATP channel triggers opioid-induced delayed cardioprotection: Circ Research 91: 186-188, 2002.

Schultz, J.E., Hsu, A.K., Gross, G.J. Morphine mimics the cardioprotection effect of ischemic preconditioning via glibenclamide-sensitive mechanism in the rat heart. Cir Res 78:1100-04, 1996.

Schultz, J.E. Hsu, A.K., Gross, G.J. Ischemic preconditioning and morphine-induced cardioprotection involve the delta-opioid receptor in the intact rat heart. J Mol Cell Cardio. 29:2187-95, (1997).

Schultz, J., Hzu, A., Nasase, H., Gross, G.J. TAN-67, a δ1-opioid receptor agonist reduces infarct size via activation of G i/o proteins and KATP channels. Am J Physiol. 274: H909-14, 1998.

Schultz., J.E., Rose E., Yao, Z., Gross, G.J. Evidence for involvement of opiod receptors in ischemic preconditioning in rat hearts.. Am J Physiol. 268 (H2) 157-162, 1995.

Sigg, D.C., Coles, J. A., Oeltgen, P.R., Iaizzo, P.A. Role of delta-opioid receptor agonists on infarct size reduction in swine. Am J Physiol Heart Circ Physiol. 282 (H1) 953-60, 2002.

Smith-Sonneborn, J., Gottsch, H., Cubin, E., Oeltgen, P.R., Thomas, P. Alternative strategy for stress tolerance: Opioids J. Gerontol: Biolog Sci. 59A:433-40, 2004.

Stefhano, G.B., Salzet, M., Hughes., T.K., Bilfinger, T.V. δ2 opioid receptor subtype on human vascular endothelium uncouples morphine stimulated nitric oxide release. International J Cardiol. 64:S43-51, 1998.

Summer, R.L., Zizhuang, L., Hildebrandt, D.: Effect of a Delta receptor agonist on duration of survival during hemorrhagic shock. Acad Emerg Med. 10:587-93, 2003.

Wild, K.D., T. Vanderah, H.I. Mosberg, and F. Porreca: Opioid d receptor subtypes are associated with different potassium channels. Eur. J. Pharmacol. 193: 135-136, 1991.

Yellon, D.M., Bazxter, G.A. "second window of protection" or delayed preconditioning phenomenon: future horizons for myocardial protection. J Mol Cell Cardiol. 27:1023-34, 1995.

Zhang, J., Haddad, Xia. Y. Delta-, but not mu-and kappa-opioid receptor activation protects neocortical neurons from glutamate-induced excitotoxic injury. Brain Res. 885: 143-53 (2000).

Bell, S.P., Sac, M.N., Patel, A., Opie, L.H., Yellon, D.M. δ-Opioid receptor stimulation mimics ischemic preconditioning in human heart muscle. J. Am Coll Cardiol. 36:2296-02, 2000.

Murakawa, K., Hirose, N., Takada, K., Suzuki, T., Nagase, H., Cools, A., Koshikawa, N. Deltorphin II enhances extracellular levels of dopamine in the nucleus accumbens via opioid receptor-independent mechanisms. European J. of Pharm. 491: 31-36, 2004.

Rutten, M., Govindaswami, M., Oeltgen, P., Smith-Sonneborn. Post-treatment with the novel deltorphin e, a δ-opioid receptor agonist, increases recovery and survival after severe hemorrhagic shock in behaving rats. Shock, 2007.

\* cited by examiner

COMPOSITIONS AND METHODS USEFUL FOR TREATING CIRCULATORY AND HYPOVOLEMIC SHOCK

RELATED APPLICATIONS

This application claims priority from U.S. Provisional Application Ser. No. 60/910,774 filed Apr. 9, 2007, the entire disclosure of which is incorporated herein by this reference.

GOVERNMENT INTEREST

This invention was made, in part, with government support from the US Office of Naval Research (ONR) "Opioid-like Hibernation Factors Provide Cerebral Ischemic Protection" (Account No. 4-6431). The government has certain rights in the invention.

BACKGROUND

Circulatory shock and hypovolemic shock are commonly occurring threatening pathophysiological states, which can occur secondary to trauma, hemorrhage, burns, sepsis, allergic reactions, and heart failure. Shock-like microcirculatory abnormalities are also associated with certain procedures, such as surgical procedures. Such shock, whether systemic or localized, is characterized by a reduction in blood pressure, blood flow, and/or blood volume, and can cause an insufficient supply of blood and oxygen to vital organs and tissues. This insufficient blood and oxygen supply can cause local hypoxia, ischemia, and can lead to loss of cellular and organ function and even death.

Currently-available treatments for circulatory and hypovolemic shock include forms of volume infusion. For example, the standard of care in initial management of hemorrhagic shock is rapid administration of large volumes fluids, several liters in an adult patient. A preferred fluid is Ringer's lactate, although normal saline or other similar isotonic crystalloid solutions are also used. The standard continued treatment is based on an observed response to the initial fluid therapy. Guidelines generally provide that up to 300 ml of electrolyte solution is required for each 100 ml of blood lost ("three for one" rule). For blood losses up to 30% of circulation blood volume, crystalloid alone will often suffice; however, with ongoing blood loss, or a more significant hemorrhage, prompt surgical intervention or blood therapy becomes necessary.

Over the last decade, this standard approach has been reexamined, leading to the conclusion that changes are needed in current resuscitation strategies used by first responders to trauma settings and by medical personnel in emergency rooms (ER) and intensive care units (ICU). There are multiple reasons for this conclusion.

First, the clinical trajectory of patients who develop multiple organ failure is set early in the resuscitation process (i.e., within about 6 hr of an event that creates a risk of shock, such as an injury resulting in hemorrhaging). Many patients at high risk require emergency surgery or interventional radiology, and arrive in an ICU after this time window. Although resuscitation efforts in the ICU can clearly modify the subsequent clinical course for the patient, even highly refined and individually tailored resuscitation cannot reverse the dysfunctional response that has already occurred. As such, currently-used resuscitation strategies do not adequately limit the incidence of multiple organ failure.

Second, although initial crystalloid volume loading is valuable in defining hemodynamic stability, to continue this process in the face of ongoing hemorrhaging promotes further bleeding, hemodilutes the patient, and sets the stage for hypothermia, acidosis, and coagulopathy. This syndrome is particularly problematic in patients with blunt trauma, who often have sources of bleeding that are not amenable to direct control. Failure to resuscitate these patients will, however, ultimately lead to irreversible shock. As such, currently used resuscitation strategies can actually exacerbate ischemic injury.

Third, although crystalloid resuscitation is efficacious in most patients, it produces problematic tissue edema in patients who arrive to an ICU in severe shock. These patients typically need massive fluid resuscitation to maintain intravascular volume and many develop abdominal compartment syndrome, which creates increased risks for multiple organ failure. Patients with severe torso trauma who are admitted with shock and an associated severe closed head injury are in a precarious situation. Under-resuscitation decreases cerebral perfusion pressure, which causes secondary brain injury. Excessive crystalloid administration promotes cerebral edema, which increases intracranial pressure and further decrease cerebral perfusion pressure. As such, currently used resuscitation strategies can exacerbate injury.

Fourth, shock initiates dysfunctional inflammation that causes multiple organ failure. Resuscitation is an obligatory intervention to decrease the severity of the shock insult, but current strategy is not directed at modulating inflammation, in fact, it may worsen it. Laboratory studies show that lactated Ringer's solution activates neutrophils. Even more disturbing is an observation that blood transfusion contains proinflammatory mediators that both prime and activate neutrophils. As such, currently used resuscitation strategies can exacerbate injury.

Prospective randomized controlled trials studying currently-used resuscitation strategies (crystalloid and colloid resuscitation) were conducted in the 1970s and 1980s, before the recognition of abdominal compartment syndrome as an important clinical entity. Additionally, albumin was the principal colloid used, but other types of colloid, such as starches and gelatins, are available and are now being used in resuscitation. Because of their higher molecular weights, colloids such as starches and gelatins are confined to the intravascular space, and their infusion results in more efficient plasma volume expansion. In severe hemorrhagic shock, however, the permeability of capillary membranes increases, allowing colloids to enter the interstitial space, which can then worsen edema and impair tissue oxygenation. Although it has been suggested that these high-molecular-weight agents could plug capillary leaks that occur during neutrophil-mediated organ injury, it has not been established that such a benefit could result from their use.

It has also been proposed that resuscitation with albumin induces renal failure and even impairs pulmonary function. Similarly, hetastarch has been shown to induce renal dysfunction in patients with septic shock and in recipients of kidneys from brain-dead donors. Hetastarch also has a limited role in massive resuscitation because it causes a coagulopathy and hyperchloremic acidosis due to its high chloride content. A new hydroxyethyl starch (HES) preparation (e.g., HEXTEND®) purportedly does not cause these adverse effects, but has not been studied in massive resuscitation. It is now thought that colloids might reduce the incidence of abdominal compartment syndrome, but this possible benefit must be weighed against the potentially detrimental effects of colloids already reported.

Results of numerous studies indicate that HES administration can lead to reduction in circulating factor VII and von Willebrand factor levels, impairment of platelet function, prolongation of partial thromboplastin time and activated partial thromboplastin time, and increase in bleeding complications. Coagulopathy and hemorrhage associated with HES are often encountered in cardiac surgery, a setting in which susceptibility to such complications is heightened by transient acquired platelet dysfunction resulting from the procedure. Thus, in cardiac surgery studies with albumin as the control, HES has resulted in platelet depletion and dysfunction, prothrombin time and activated partial thromboplastin time prolongation, and increased postoperative bleeding. Dextran, as compared with albumin, has been shown to reduce platelets and increase postoperative bleeding in cardiac surgery patients. Postoperative blood loss was early correlated with the volume of gelatin used to prime the extracorporeal circuit. Artificial colloids, including dextran, hetastarch and pentastarch, have been associated with renal impairment, and HES has been demonstrated to increase sensitive markers of renal tubule damage in surgical patients. In a study of sepsis patients, HES exposure was recently shown to be an independent risk factor for acute renal failure. In the renal transplantation setting, HES has been found to reduce urinary output, increase creatinine levels and dopamine requirement, and increase the need for hemodialysis or hemodiafiltration.

Studies have suggested that both over- and under-resuscitation can increase mortality. Early aggressive fluid resuscitation can be deleterious, according to a clinical trail in which mortality was reduced by delaying fluid therapy. Also, there are several practical and logistic limitations to the current methods of prehospital resuscitation, which include limitations on the amount of fluid that can be delivered due to inadequate i.v. bore size and limited availability of fluid in the field, e.g. combat casualty care. Hypotensive resuscitation is one approach that has been advocated as a better means to perform field resuscitation of penetrating trauma. However, early application of aggressive resuscitation has been shown to affect outcomes deleteriously in animal models of uncontrolled hemorrhage, in which aggressive resuscitation using a variety of fluids caused rapid increases in blood pressure, internal bleeding, and higher mortality.

In the early 1980s research interest in hypertonic saline was spurred. Small-volume hypertonic saline was shown to be as effective as large-volume crystalloids in expanding plasma volume and enhancing cardiac output in hemorrhagic shock in animals. Furthermore, hypertonic saline increased perfusion of the microcirculation, presumably by selective arteriolar vasodilation and by decreasing swelling of red blood cells and of the endothelium. This improved microcirculation, however, could lead to increased bleeding. Consequently, hypertonic saline was tested in animal models of uncontrolled hemorrhagic shock and was shown to increase bleeding, but mortality was model-dependent and the best survival was obtained when saline was given with high-volume crystalloids. Additionally, the resuscitative effectiveness of hypertonic saline was found to be enhanced by combination with dextran (hypertonic saline dextran (HSD)). In view of the small volume needed to achieve these effects, there was great interest in the use of these fluids in resuscitation in the field for both military and civilian use.

From the late 1980s through the early 1990s, several trials were done. Individually, these trials found survival outcome to be inconsistently improved, but did document that a bolus of hypertonic saline or HSD was safe. Meta-analysis of these data suggests that hypertonic saline is no better than standard of care isotonic crystalloid fluids, but that HSD might be better. Subgroup analysis showed that patients who presented with shock and concomitant severe closed head injury benefited most from HSD. This observation was consistent with laboratory data showing that, compared with isotonic crystalloid, hypertonic saline or HSD increases cerebral perfusion pressure, decreases intracranial pressure, and decreases brain edema, in combined head injury and hemorrhagic shock. This finding has led some authorities to recommend that hypertonic saline should replace mannitol in the management of intracranial hypertension in patients with severe closed head injury. The argument in favor of hypertonic saline is even more compelling with the recent recognition that hypertonic saline resuscitation decreases the inflammatory response (specifically neutrophil cytotoxicity) in animal models of hemorrhagic shock, ischemia and reperfusion, and sepsis.

More recent studies have compared hypotensive and normotensive resuscitation of hemorrhage using lactated Ringer's (LR) with hypotensive resuscitation using HEXTEND® (Hex) 6% hetastarch in isotonic buffered saline in a multi-hemorrhage sheep model. Hypotensive resuscitation with LR greatly reduced volume requirements as compared with normotensive resuscitation, and Hex achieved additional volume sparing. However, trends toward lower base excess (BE) values and low levels of urinary flow in some animals in both hypotensive treatment protocols and the occurrence of deaths only in the hypotensive treatment protocols suggest that resuscitation to a target MAP of 65 mmHg may be too low for optimal outcomes. Hypotensive resuscitation regimens may reduce bleeding but do not optimally restore metabolic function.

To summarize, currently-available treatments for circulatory and hypovolemic shock focus on various forms of volume infusion. Intravenous fluids appear to improve hemodynamic indices in the short term, but most also have adverse consequences on hemostatic mechanisms. Indeed, it is now becoming clear that resuscitation fluids may actually potentiate cellular injury via severe immune activation and upregulation of cellular injury markers that can result in exacerbation of blood loss. Bleeding can also be enhanced by injudicious fluid administration as a consequence of dilutional coagulopathy and secondary clot disruption from increased blood flow, increased perfusion pressure, and decreased blood viscosity.

Accordingly, there remains a need in the art for a method of treating circulatory and hypovolemic shock, which avoids the above-identified problems.

SUMMARY

The present invention meets some or all of the above-identified needs, as will become evident to those of ordinary skill in the art after a study of information provided in this document. This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The present invention relates to the use of an isolated polypeptide, compositions and methods for treating shock associated with a reduction of blood volume, or an insufficient supply of blood to an organ or tissue. The method allows bleeding to be controlled, while providing effective hemodynamic and metabolic support. The method can be practiced without making use of resuscitation fluids, which have been associated with various disadvantages and risks. The method of the present invention can be used for treating shock that is characterized by a state of whole body ischemia. The method of the present invention can be used for treating circulatory and hypervolemic shock, such as hemorrhagic shock, and injuries resulting from such shock, such as injuries to an organ or tissue due to an inadequate supply of oxygen being delivered to the organ or tissue.

Disclosed herein is an isolated polypeptide, comprising the amino acid sequence Tyr-(D-Ala)-Phe-Ala-Ile-Gly-Asp-Phe-Ser-Ile-$NH_2$ (SEQ ID NO: 1), which is referred to herein as Deltorphin-E or Delt-E. Amino acids can occur in two possible optical isomers, D isomers and L isomers. D-Ala refers to a D-isomer of alanine. Also disclosed herein is a biologically active Deltorphin-E polypeptide, including an amino acid sequence having at least about 90% or greater homology to SEQ ID NO: 1. Also disclosed herein is a biologically active Deltorphin-E polypeptide, including an amino acid sequence encoded by a nucleic acid sequence having at least about 90% or greater homology to the nucleic acid sequence $TAn_1$ $GCn_3$ $TTn_1$ $GCn_3$ $ATn_2$ $GGn_3$ $GAn_1$ $TTn_1$ $AGn_1$ $ATn_2$ (SEQ ID NO: 2), where $n_1$ is T or C; $n_2$ is T, C, or A; and $n_3$ is T, C, A, or G. Also disclosed herein are pharmaceutical compositions, including a pharmaceutically effective amount of a Deltorphin-E polypeptide, and a pharmaceutically acceptable carrier.

An exemplary method of the present invention includes administering an effective amount of a Deltorphin-E polypeptide in a pharmaceutically acceptable formulation. The polypeptide can be administered concurrently with or before the onset of shock or the occurrence of an event that creates a risk of shock. The polypeptide can be administered up to about 24 hours before the onset of shock or the occurrence of the event. The polypeptide can be administered subsequent to the onset of shock or the occurrence of an event that creates a risk of shock. The polypeptide can be administered up to about 4 hours subsequent to the occurrence of an event that creates a risk of shock.

The event creating a risk of shock can be, for example, hemorrhage or a planned surgery. Examples of planned surgeries include planned ischemia, heart valve replacement surgery, coronary artery bypass graft surgery, stint placement surgery, orthopedic surgery, organ repair surgery, organ transplantation surgery, and a surgery to implant a device.

An effective amount of the polypeptide can be administered in accordance with an exemplary method such that one or more desired effects are produced. A desired effect can be a prophylactic effect. A desired effect can be a therapeutic effect. In certain embodiments, treatment using the polypeptide can produce one or more prophylactic effects and one or more therapeutic effects. Examples of prophylactic effects include preventing or reducing the risk of shock, and preventing or reducing the risk of injuries resulting from shock. Examples of therapeutic effects include curing or mitigating shock, and restoring perfusion to organs and tissues.

BRIEF DESCRIPTION OF THE SEQUENCE LISTING

Figure 1:
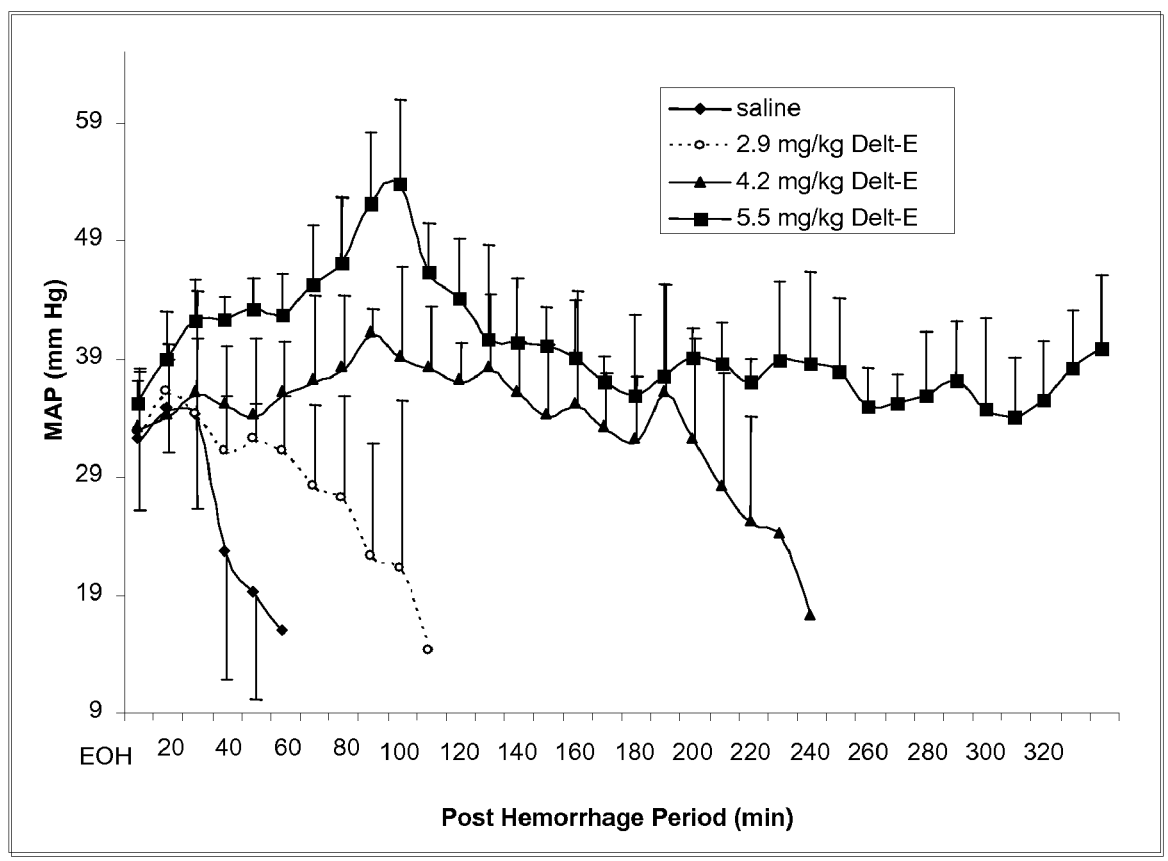
FIG. 1 is a graph comparing dose-dependent recovery of mean arterial pressure (MAP, mmHg) as a function of time for Delt-E-treated groups and control group, where treatment was immediately after severe hemorrhage.

SEQ ID NO: 1 is an isolated polypeptide Deltorphin-E (Delt-E), including the following amino acid sequence: Tyr-(D-Ala)-Phe-Ala-Ile-Gly-Asp-Phe-Ser-Ile-$NH_2$.

SEQ ID NO: 2 is an isolated nucleic acid molecule, including the following nucleic acid sequence: $TAn_1$ $GCn_3$ $TTn_1$ $GCn_3$ $ATn_2$ $GGn_3$ $GAn_1$ $TTn_1$ $AGn_1$ $ATn_2$, where $n_1$ is T or C; $n_2$ is T, C, or A; and $n_3$ is T, C, A, or G.

DESCRIPTION OF EMBODIMENTS OF THE INVENTION

The details of one or more embodiments of the present invention are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the following terms are believed to be well understood by one of ordinary skill in the art, the following definitions are set forth to facilitate explanation of the present invention.

Unless defined otherwise, all technical and scientific terms used herein have the same meaning as commonly understood by one of ordinary skill in the art. Although any methods, devices, and materials similar or equivalent to those described herein can be used in the practice or testing of the presently-disclosed subject matter, representative methods, devices, and materials are now described.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "biologically active" refers to an ability to affect treatment for the disease state being treated when provided in an effective amount.

As used herein, the terms "effective amount" and "therapeutically effective amount" are used interchangeably and mean a dosage sufficient to provide treatment for the disease state being treated. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of ordinary skill in the art using only routine experimentation.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) *Nucleic Acid Res* 19:5081; Ohtsuka et al. (1985) *J Biol Chem* 260: 2605-2608; Rossolini et al. (1994) *Mol Cell Probes* 8:91-98). The terms "nucleic acid" or "nucleic acid sequence" can also be used interchangeably with gene, open reading frame (ORF), cDNA, and mRNA encoded by a gene.

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein," "polypeptide," and "peptide" are used interchangeably herein when referring to a gene product. Unless otherwise indicated, a particular polypeptide also implicitly encompasses conservatively-substituted variants thereof.

The term "conservatively substituted variant" refers to a polypeptide comprising an amino acid residue sequence substantially identical to the sequence of a polypeptide whose sequence is disclosed herein, in which one or more residues have been conservatively substituted with a functionally-similar residue, and which is biologically active. The phrase "conservatively-substituted variant" also includes polypeptides wherein a residue is replaced with a chemically-derivatized residue, provided that the resulting polypeptide is biologically active. Examples of conservative substitutions include the substitution of one non-polar (hydrophobic) residue, such as isoleucine, valine, leucine, or methionine for another; the substitution of one polar (hydrophilic) residue for another, such as between arginine and lysine, between glutamine and asparagine, between glycine and serine; the substitution of one basic residue such as lysine, arginine, or histidine for another; or the substitution of one acidic residue, such as aspartic acid or glutamic acid for another.

The term "isolated", when used in the context of an isolated polypeptide, is a polypeptide that, by the hand of man, exists apart from its native environment and is therefore not a product of nature. An isolated polypeptide can exist in a purified form or can exist in a non-native environment such as, for example, in a transgenic host cell.

Disclosed herein are polypeptides, compositions, and methods useful for treating shock associated with a reduction of blood volume, or an insufficient supply of blood to an organ or tissue. For example, the compositions and methods of the present invention may be used for treating circulatory and hypovolemic shock, such as hemorrhagic shock, and injuries resulting from such shock, such as injuries to an organ or tissue due to an inadequate supply of oxygen being delivered to the organ or tissue.

The present invention includes an isolated Deltorphin-E (Delt-E) polypeptide, comprising the amino acid sequence Tyr-(D-Ala)-Phe-Ala-Ile-Gly-Asp-Phe-Ser-Ile-NH$_2$ (SEQ ID NO: 1). Amino acids can occur in two possible optical isomers, D isomers and L isomers. D-Ala refers to a D-isomer of alanine. In certain embodiments, Delt-E has a molecular weight of about 1102.3 daltons. In certain embodiments, a biologically active Deltorphin-E polypeptide includes an amino acid sequence having at least about 90% or greater homology to SEQ ID NO: 1. In certain embodiments, a biologically active Deltorphin-E polypeptide includes an amino acid sequence encoded by a nucleic acid sequence having at least about 90% or greater homology to the nucleic acid sequence TA$n_1$ GC$n_3$ TT$n_1$ GC$n_3$ AT$n_2$ GG$n_3$ GA$n_1$ TT$n_1$ AG$n_1$ AT$n_2$ (SEQ ID NO: 2), where $n_1$ is T or C; $n_2$ is T, C, or A; and $n_3$ is T, C, A, or G. The Deltorphin-E polypeptide can be produced by a number of methods known to those skilled in the art, such as methods using an automated peptide synthesizer or through recombinant molecular biology techniques.

The present invention includes compositions comprising a pharmaceutically effective amount of a Deltorphin-E polypeptide, and a pharmaceutically acceptable carrier. Exemplary compositions can include a pharmaceutically acceptable carrier. Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The compositions can take such forms as suspensions, solutions or emulsions in oily or aqueous vehicles, and can contain formulatory agents such as suspending, stabilizing and/or dispersing agents. Alternatively, Delt-E can be in powder form for constitution with a suitable vehicle before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

In certain embodiments, Delt-E can be formulated for administration in an aqueous-based liquid, such as phosphate-buffered saline, to form an emulsion. For example, Delt-E can be solubilized in a solution including ethanol, propylene glycol, and 1N NaOH in a 1:1:1 ratio, or formulated in an organic liquid such as hydroxy-propyl-beta-cyclodextrin to form a solution. An appropriate amount of Delt-E can be solubilized in about 100 µl of the ethanol/propylene glycol/NaOH solution or hydroxy-propyl-beta-cyclodextrin. A desired concentration of Delt-E can be obtained by adding sterile physiological saline, phosphate buffered saline, or lactated Ringer's solution. The initial alkaline pH can be adjusted to a desired pH using, for example, 1N HCl. The pH can be adjusted to between about 7.35 and about 7.45, or about 7.4.

The present invention includes methods for treating shock associated with a reduction of blood volume, or an insufficient supply of blood to an organ or tissue using Delt-E. For example, states of whole body ischemia, as occurs in hemorrhagic shock, can be treated using methods of the present invention. For another example, methods of the present invention can be used to provide extended pharmacological ischemic preconditioning (PPC) in hemorrhagic shock. The methods can be practiced without the use of volume infusion (i.e., without the use of resuscitation fluids).

For purposes of simplicity, when the term "shock" is used herein, unless otherwise indicated, it is used to describe circulatory or ischemic shock, hypervolemic shock, hemorrhagic shock, or other types of shock associated with a reduction of blood volume in an organ or tissue, or an insufficient supply of blood to an organ or tissue.

Shock that can be treated in accordance with the present invention can occur in a number of situations. For example, an event that creates a risk of shock can occur in civilian and military trauma settings, such as hemorrhage creating a risk of hemorrhagic shock. For another example, an event such as a planned surgery can create a risk of shock. Examples of such surgeries include, heart valve replacement surgeries, coronary artery bypass graft surgeries, stint placement surgeries, orthopedic surgeries, organ repair surgeries, organ transplantation surgeries, surgeries to implant devices, and the like.

An exemplary method of the present invention for treating shock in a subject includes administering an effective amount of Delt-E to the subject. As used herein, the term "subject" includes both human and animal subjects. Thus, the disclosed methods can have veterinary therapeutic uses. As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

Treatment can be affected in accordance with the present invention before, concurrently with, or after an event that creates a risk of shock, such as hemorrhage. Treatment can be affected in accordance with the present invention before, concurrently with, or after the shock occurs. Desired effects of treatment can include therapeutic effects and prophylactic effects.

For example, if the treatment is affected before the event creating a risk of shock occurs, the treatment can be intended to produce prophylactic effects. For another example, if the treatment is affected concurrently with or after the event creating a risk of shock occurs, the treatment can also be intended to produce prophylactic effects. In such cases, treatment could be intended to prevent or reduce the risk of shock, and/or prevent or reduce the risk of injuries resulting from such shock.

For another example, if the treatment is affected concurrently with or after the shock occurs, the treatment can be intended to produce prophylactic and therapeutic effects, preventing or reducing injuries resulting from shock, and curing or mitigating the shock, e.g., restoring mean arterial pressure and perfusion of organs and tissues.

The methods of the present invention can make use of Delt-E and compositions containing Delt-E, and are useful in a variety of settings. For example, Delt-E treatment is useful in clinical settings where planned surgeries are performed, including planned ischemia and other procedures. In this regard, it can be desirable to treat a subject who will undergo a planned ischemia or surgical procedure, prior to the occurrence of the procedure, because such procedures can result in hemorrhage, ischemia, and/or shock, i.e., affecting treatment before an event that creates a risk of shock using Delt-E as a pharmacological ischemic preconditioning agent where ischemic events can be anticipated. Depending on the status of a subject undergoing a procedure, medical personnel could treat that subject after the procedure has been initiated, for example, when a risk of hemorrhage becomes apparent. For another example, Delt-E treatment is useful in an emergency room (ER) or an intensive care unit (ICU) setting. For another example, Delt-E treatment is useful in civilian trauma settings, e.g., highway accident scenes, or military trauma settings. In this regard, Delt-E could be rapidly administered by first responders during the initial period following trauma, when lifesaving intervention is often considered most critical. Depending on the status of a subject being treated in a trauma setting, a first responder could treat that subject before the onset of shock, concurrently with the onset of shock, or after the onset of shock. Since large volumes of resuscitation fluids, which are associated with known methods of treatment, would not be required when administering Delt-E, the method of the present invention is especially useful in a civilian or military trauma setting, where large fluid volumes would be difficult to obtain, transport, or access.

Delt-E can be administered prior to the onset of shock or prior to the occurrence of an event that creates a risk of shock, e.g., planned surgery. For example, in some embodiments, Delt-E can be administered up to about 24 hours prior to the onset of shock or prior to the occurrence of an event that creates a risk of shock. In some embodiments, Delt-E can be administered up to about 1, 2, 3, 4, 5, 10, 15, or 20 hours prior to the onset of shock or prior to the occurrence of an event that creates a risk of shock. Further, in some embodiments, Delt-E can be administered about 20 to about 24 hours prior to the onset of shock or prior to the occurrence of an event that creates a risk of shock. In some embodiments, Delt-E can be administered about 15 to about 20 hours, about 10 to about 15 hours, about 5 to about 10 hours, about 4 to about 5 hours, about 3 to about 4 hours, about 2 to about 3 hours, or about 1 to about 2 hours prior to the onset of shock or the occurrence of an event that creates a risk of shock.

Delt-E can be administered up to about 4 hours subsequent to the onset of shock or the occurrence of an event that creates a risk of shock. Delt-E can be administered up to about 1, 2, or 3 hours subsequent to the onset of shock or the occurrence of an event that creates a risk of shock. Delt-E can be administered concurrently with the onset of shock or the occurrence of an event that creates a risk of shock.

Delt-E can be administered in accordance with the present invention in a variety of manners. A solution or an emulsion of Delt-E can be administered parenterally. A solution or an emulsion of Delt-E can be administered by intravenous injection, intraperitoneal injection, or intraarterial injection. A solution or an emulsion of Delt-E can be administered by direct injection into the brain, for example, intracerebroventricular injection, for dispersion to other areas. Injection volumes can be about 0.5 to about 2.0 milliliters. Delt-E can be administered in combination with other compounds, if desired.

Actual dosage levels of Delt-E can be varied so as to administer an amount of Delt-E that is effective to achieve the desired therapeutic response for a particular subject and/or application. The selected dosage level will depend upon a variety of factors including the activity of the therapeutic composition, formulation, the route of administration, combination with other drugs or treatments, severity of the condition being treated, the physical condition and prior medical history of the subject being treated, and the like. Preferably, a minimal dose is administered, and dose is escalated in the absence of dose-limiting toxicity to a minimally effective amount. Determination and adjustment of a therapeutically effective dose, as well as evaluation of when and how to make such adjustments, are known to those of ordinary skill in the art of medicine, and any necessary determinations in a particular case can be made by those of ordinary skill in the art using only routine experimentation.

For administration of a composition as disclosed herein, conventional methods of extrapolating human dosage based on doses administered to a murine animal model can be carried out using the conversion factor for converting the mouse dosage to human dosage: Dose Human per kg=Dose Mouse per kg×12 (Freireich et al., (1966) Cancer Chemother Rep. 50:219-244). Drug doses can also be given in milligrams per square meter of body surface area because this method, rather than body weight, achieves a good correlation to certain metabolic and excretionary functions. Moreover, body surface area can be used as a common denominator for drug dosage in adults and children as well as in different animal species as described by Freireich et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m².

In certain embodiments, useful doses of Delt-E are from about 1 µg/kg to about 20 mg/kg of body weight of the subject being treated. In certain embodiments of the invention, useful doses of Delt-E are from about 1-1000 µg/kg. In certain embodiments of the invention, useful doses of Delt-E are: from about 1 µg/kg to about 200 µg/kg, from about 200 µg/kg to about 250 µg/kg, from about 250 µg/kg to about 500 µg/kg, from about 500 µg/kg to about 750 µg/kg, from about 750 µg/kg to about 1000 µg/kg, from about 1 mg/kg to about 2 mg/kg, from about 2 mg/kg to about 3 mg/kg, from about 3 mg/kg to about 5 mg/kg, from about 5 mg/kg to about 10 mg/kg, from about 10 mg/kg to about 15 mg/kg, and from about 15 mg/kg to about 20 mg/kg.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, N.J.; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Fla.; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pa.; and Speight et al., (1997) Avery's Drug Treatment: A Guide to the Properties Choice, Therapeutic Use and Economic Value of Drugs in Disease Management, 4th ed. Adis International, Auckland/Philadelphia; Duch et al., (1998) Toxicol. Lett. 100-101:255-263.

The present invention is further illustrated by the following specific but non-limiting examples. The following examples may include compilations of data that are representative of data gathered at various times during the course of development and experimentation related to the present invention.

EXAMPLES

A murine hemorrhagic shock model was used to evaluate the effects of administration of Deltorphin-E (Delt-E), without concomitant fluid resuscitation, on hemodynamic status, plasma lactate levels, and survival rates.

Study Design: Post Hemorrhage Delt-E Infusion

The hemorrhagic shock model used was a volume-controlled model similar to that of Summers et al. Acad Emerg Med. 10:587-93 (2003). Forty-six male Sprague-Dawley rats (about 341-411 grams) were acclimated to a laboratory environment for a week. In dwelling heparinized PE 10 catheters were placed in the femoral artery and the femoral vein of anesthetized rats. The two catheters were combined and exited suprascapularly, tied in place with braided silk, and covered with a piece of hypoallergenic mesh to prevent kinking. Rats were then placed in recovery cages for 24 hr, allowed access to food and water, and allowed unrestricted access to both catheters. The femoral artery catheter was used for volume-controlled hemorrhage and blood pressure measurements and the femoral vein catheter was used for Delt-E infusion. Each selected animal was randomly assigned 1 of 6 post hemorrhage treat groups: 1 mL/100 g saline control (n=6), 2.85 mg/kg Delt-E (n=6), 4.2 mg/kg Delt-E (n=6), 5.5 mg/kg Delt-E (n=6), and 14 mg/kg Delt-E (n=6). Animals were also selected and randomly assigned to 1 of 4, 30-minute pre-treatment inhibitor groups: Naltriben Methane Sulfonate (NTB) (n=4), Naltrexone (n=4), Glibenclamide (n=4), and 7-Dehydrobenzylidine naltrexone (BNTX) (n=4) followed by a 5.5 mg/kg injection of Delt-E.

Treatment: Twenty-four hours after catheter placement, test rats (n=24) were infused in the femoral vein with either 2.85, 4.2, 5.5 or 14 mg/kg of Delt-E (Tyr-D-Ala-Phe-Ala-Ile-Gly-Asp-Phe-Ser-Ile-NH$_2$; SEQ ID NO: 1) dissolved in 1.0 ml Lactated Ringers (LR) solution pH 7.4. Control rats (n=6) were infused with 1.0 ml Lactated Ringers solution pH 7.4. Prior to hemorrhage MAP and HR were recorded to establish baseline levels. During hemorrhage approximately 48% of the total blood volume was removed at a rate of 3 mL/100 g over a 9- to 11-minute period. After the final mL of blood was removed the various venous catheter treatment injections were administered, MAP and HR were recorded continuously for the duration of survival or up to 6 hours.

Biomarker protocols: Survival time was determined by the post hemorrhage time after injection until death, or a predetermined 360 minute survival interval. Death was defined as systolic blood pressure without pulsation, and apnea. Animals were observed for several more minutes to ensure that autoresuscitation did not occur. Any animal surviving 360 minutes was sacrificed according to our protocol with urethane (1.0 g/kg, Sigma Aldrich). This was done to minimize any discomfort to the animal and also because reportedly D-Alanine deltrophins exhibit plasma half-lives of six hours (Marastoni et al. 1991). Plasma lactate levels were determined from arterial samples at the beginning of hemorrhage (BOH) and 10 min after end of hemorrhage (EOH) and venous catheter injection utilizing a Vitros® 950 Chemistry Analyzer (Ortho-Clinical Diagnostics, Rochester, N.Y.). Pulse pressure was determined by the difference (mmHg) between the systolic and diastolic pressure during a single cardiac cycle. A total of six measurements for each treatment group were taken after venous catheter injection at a frequency of one every five minutes for first 30 minutes.

Opioid Inhibitors: The opioid inhibitors (naltrexone, naltriben methane sulfonate (NTB) and 7 Dehydrobenzylidine naltrexone (BNTX) and Glibenclamide were administered 30 minutes prior to hemorrhage. MAP and HR were recorded continuously before hemorrhage to ensure no adverse affects on MAP or HR occurred as a result of the pre-injection. At the end of 30 minutes, volume-controlled hemorrhage was induced followed by a post hemorrhage injection of 5.5 mg/kg Delt-E, the optimal dose found to increase hemodynamic stability. Naltrexone (10 mg/kg, Sigma-Aldrich), NTB (1 mg/kg, Sigma-Aldrich), and BNTX (1 mg/kg, Tocris Bioscience) were used as 30 minute pre-injection opioid receptor antagonists. Glibenclamide (10 mg/kg, Sigma Aldrich) was used as a $K_{ATP}$ channel blocker.

Data Analysis: Statistical analysis was preformed using SPSS software with P value <0.05 being considered significant. The survival, MAP, HR and lactic acid values were analyzed using repeated measures analysis of variance (ANOVA) between groups to identify differences between groups. To evaluate differences between means, the ANOVA with post hoc least square differences were used (LSD analysis).

The steady state changes in MAP and HR were fitted to a sigmoid logistic equation, plotted, and derivative of the equation were used to obtain the upper and lower plateaus and create curves that reflect instantaneous change as well as the $BP_{50}$, the MAP halfway between upper and lower plateaus (Flynn F W and Stricker 2003; Head and McCarty 1987, McBride et al., 2005) were employed. The average heart rate gain, or slope of the curve between the upper and lower inflection points was derived from coefficients of the logistic equation and reflects the greatest sensitivity of the baroreflex (Head and McCarty 1987).

Results: The MAP at the beginning (112±1.9 mmHg) or end (33±0.63 mmHg) of hemorrhage was not significantly different between any of the treatment groups using repeated-measures ANOVA. With reference to FIG. 1, the 5.5 mg/kg Delt-E post treatment group was significantly (P<0.01) higher when compared with the saline control group during the entire interval examined. The 14.0 mg/kg dose of Delt-E was found to be toxic and thus is excluded from all figures as seen in Table 1. With reference to FIG. 1 and Table 1, the max MAP recorded during recovery post hemorrhage was significantly higher for 2.9 mg/kg (P<0.05), 4.2 mg/kg (P<0.05), and 5.5 mg/kg (P<0.01) treated Delt-E group versus the saline control group, 50±17 mmHg, 53±11 mmHg, and 58±7 mmHg vs. 35±9 mmHg respectively. However, mean heart rate trended downward for both groups with no significant difference in heart rate between the control group and any Delt-E treated group.

TABLE 1

Delt-E Dose Response Comparison of Hemodynamic Biomarkers.

| Group (n) (dose) | Survival Time in minutes ± S.E. | Maximum MAP in mmHg ± S.E. | Maximum HR in BPM ± S.E. |
|---|---|---|---|
| Saline (6) (1 mL/100 g control) | 50 ± 8 | 35 ± 9 | 425 ± 94 |
| Delt-E (6) (2.9 mg/kg) | 107 ± 11** | 50 ± 17* | 432 ± 79 |
| Delt-E (6) (4.2 mg/kg) | 232 ± 14** | 53 ± 11* | 403 ± 65 |
| Delt-E (6) (5.5 mg/kg) | 331 ± 18**†† | 58 ± 7** | 396 ± 40 |
| Delt-E (6) (14.0 mg/kg) | 27 ± 7 | 51 ± 15* | 394 ± 79 |

††Rats sacrificed at six hours.
*P < 0.05 compared with saline controls
**P < 0.01 compared with saline controls.
(n) = number of animals per treatment group
Legend: MAP = mean arterial pressure and BPM = beats per minute.
Repeated-measures ANOVA revealed statistically significant differences in survival time distributions, and maximum MAP distributions between the control and Delt-E groups. Post-Hoc measurements showed significant increase in survival time in both the 4.2 mg/kg and 5.5 mg/kg Delt-E treated groups. MAP was also significantly improved in both the 4.2 and 5.5 mg/kg Delt-E treated group. There was no significance difference seen in the Heart Rate maximum BPM between any of test groups.

Figure 2:
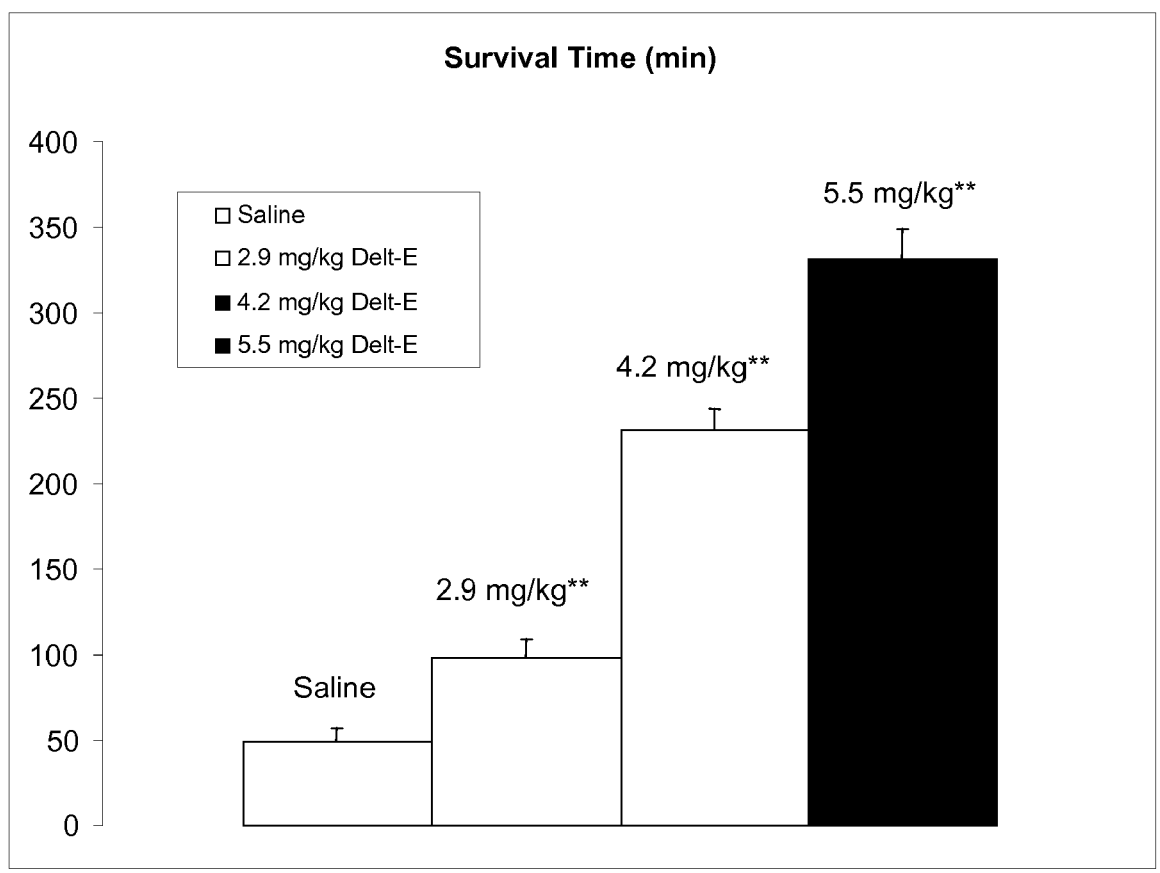
FIG. 2 is a bar graph comparing the time of survival for Delt-E-treated groups at three different doses and control group, where treatment was immediately after severe hemorrhage.

With reference to FIG. 2 and Table 1, repeated-measures ANOVA revealed a significant (P<0.01) increase in survival time for the 2.9 mg/kg, 4.2 mg/kg, and 5.5 mg/kg Delt-E treated group versus the control group (107±1 min, 232±14 min, and 331±18 min vs. 50±8 min, respectively.

Figure 3:
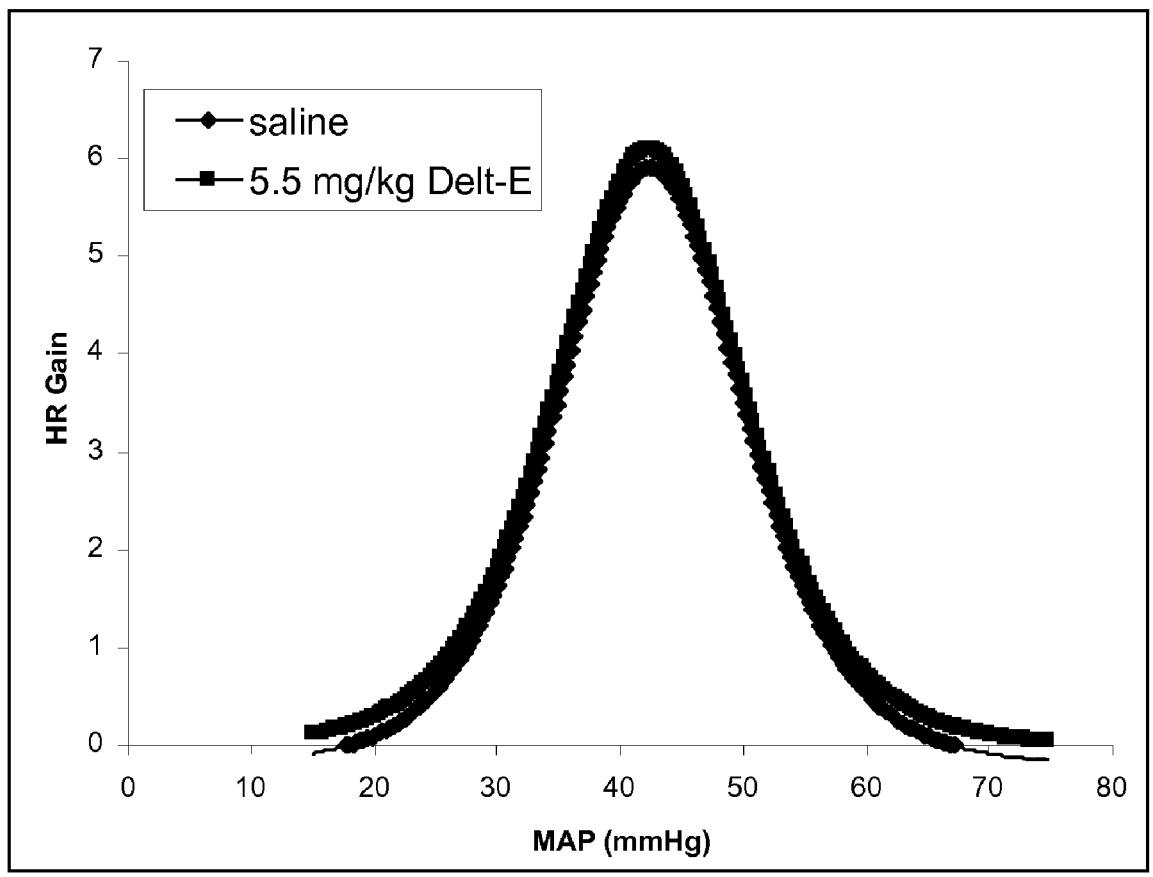
FIG. 3 is a graph of the average heart rate gain post-severe hemorrhage after treatment with saline or 5.5 mg/kg Delt-E.

With reference to FIG. 3, Delt-E did not significantly alter the average $BP_{50}$ or average HR gain at the 5.5 mg/kg Delt-E dose. The 5.5 mg/kg Delt-E dose is the most effective in restoring hemodynamic parameters post hemorrhage when compared with saline.

Figure 4:
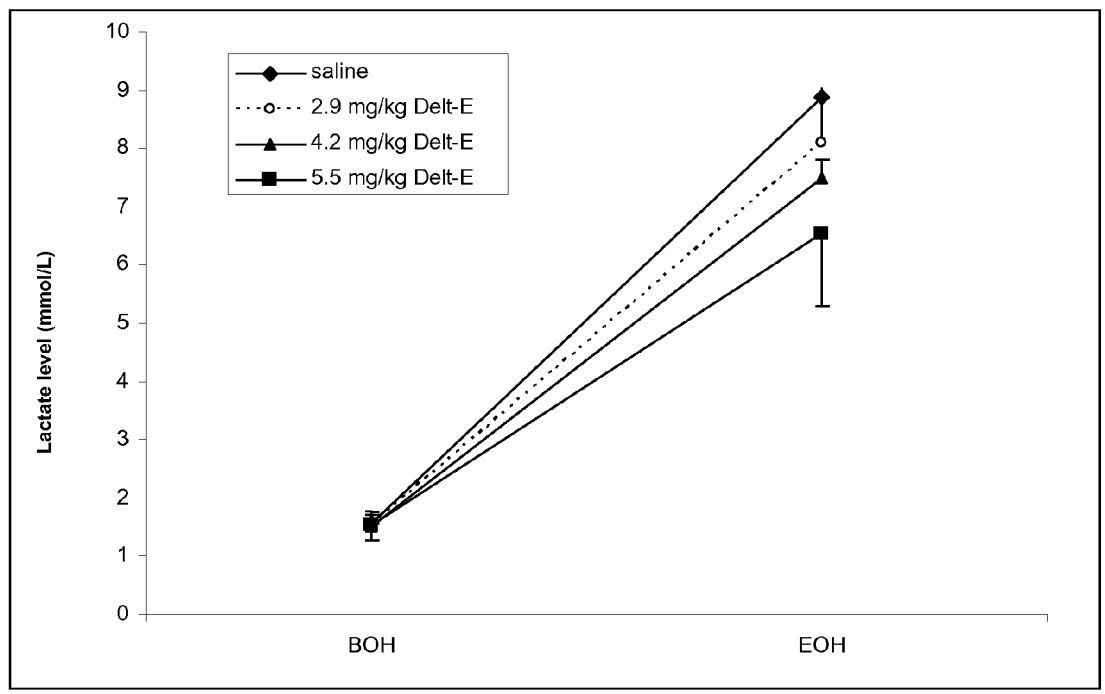
FIG. 4 is a graph comparing lactate levels (mmol/l), in arterial blood sampled at the beginning and end of hemorrhage for control group and Delt-E-treated groups at three different doses where treatment was immediately after severe hemorrhage.

With reference to FIG. 4, mean lactic acid levels at the end of hemorrhage for saline controls increased 6-fold to 8.88±0.1 mmol/L, and four-fold for 5.5 mg/kg Delt-E treated animals to 6.54±1.54 mmol/L. The 5.5 mg/kg Delt-E treated group was the only group that had a significantly lower lactic acid level (p>0.01) than the saline control group.

Figure 5:
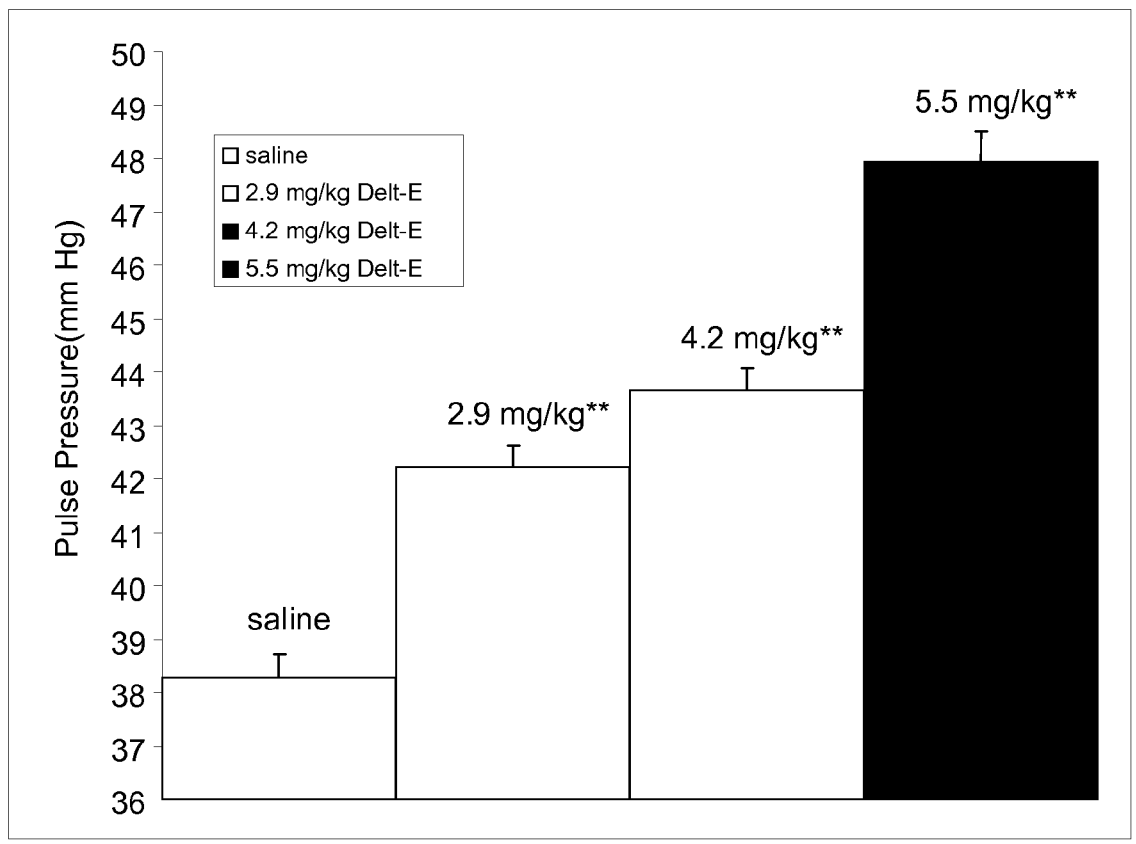
FIG. 5 is a bar graph comparing the Delt-E dose response postinjection pulse pressure (difference between systolic and diastolic pressure).

With reference to FIG. 5, post hemorrhage injections of Delt-E significantly (P<0.01) increased pulse pressure (mmHg systolic-mmHg diastolic) for the 2.9 mg/kg, 4.2 mg/kg, and 5.5 mg/kg Delt-E treated group versus the saline control group (42±0.37 mmHg, 44±0.4 mmHg, and 48±0.56 mmHg vs. 38±0.44 mmHg respectively) in a dose dependent manner (P<0.01).

Figure 6:
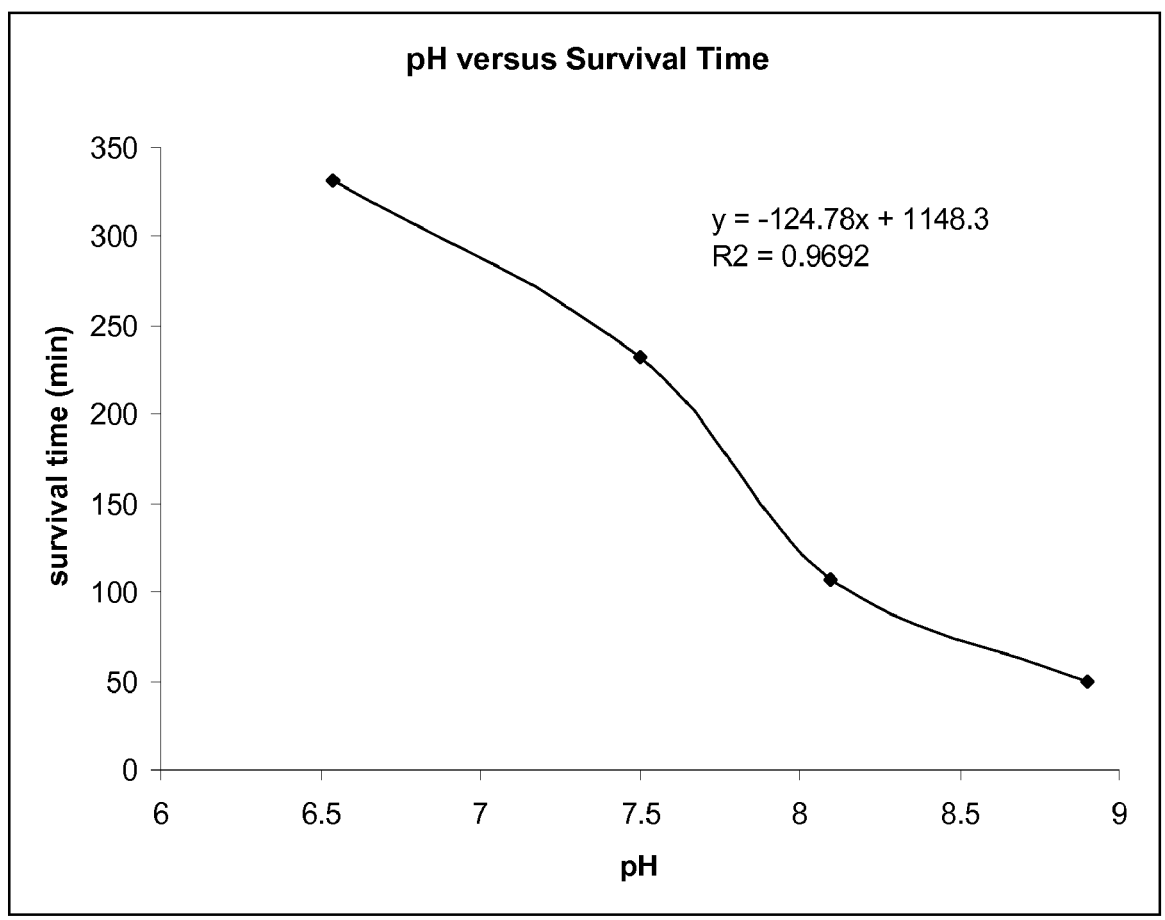
FIG. 6 is a graph of the Delt-E dose response postinjection comparison of pH versus survival time.

With reference to FIG. 6, comparison of Delt-E mediated survival time versus pH post hemorrhage showed a significant ($R^2$=0.929) dose response correlation between the decrease in pH and increase in survival time. For every 0.1 decrease in pH there is a 12.5 minute increase in survival time.

Naltrexone, the universal opioid antagonist of mu, kappa, and δ opioid receptors and the specific $δ_2$ receptor antagonist NTB blocked the post hemorrhage hemodynamic recovery benefits of 5.5 mg/kg Delt-E as seen in Table 2. BNTX the $δ_1$ specific opioid antagonist, on the other hand, did not block the 5.5 mg/kg Delt E improvement in survival and MAP recovery as seen in Table 2.

TABLE 2

Hemodynamic Biomarker Response to 30 minute Inhibitor Pre-treatment of Inhibitors Before 5.5 mg/kg Delt-E Post Hemorrhage Injection

| Group (n) (dose) | Survival Time in minutes ± S.E. | Maximum MAP in mmHg ± S.E. | Maximum HR in BPM ± S.E. |
|---|---|---|---|
| Saline (6) (1 mL/100 g control) | 50 ± 8 | 35 ± 9 | 425 ± 94 |
| NTB (4) (1 mg/kg) | 58 ± 12 | 37 ± 13 | 423 ± 68 |
| Naltrexone (4) (10 mg/kg) | 95 ± 11** | 49 ± 8* | 419 ± 75 |
| Glibenclamide (4) (10 mg/kg) | 347 ± 15**†† | 56 ± 10** | 393 ± 43 |
| BNTX (4) (1 mg/kg) | 356 ± 3**†† | 55 ± 12** | 400 ± 77 |
| Delt-E (6) (5.5 mg/kg) | 331 ± 18**†† | 58 ± 7** | 396 ± 40 |

††Rats sacrificed at six hours
*P < 0.05 compared with saline controls
**P < 0.01 compared with saline controls.
(n) = number of animals per treatment group
Legend: Repeated-measures ANOVA revealed no significant differences from controls when treatment with Naltrexone or Naltriben preceeded Delt E intervention;. However, significant differences in survival time and maximum MAP similar to Delt E alone group were found when glibenclamide or BNTX preceeded Delt E treatment. Therefore neither glibenclaminde nor BNTX interfered with the Delt E advantage. No significance difference was seen in maximum BPM between any of the test groups. *P < 0.05. **P < 0.01.

Similarly, Glibenclamide did not alter the survival advantage of post treatment with Delt E since repeated-measures ANOVA revealed no statistically significant differences in survival time distributions, and maximum MAP distributions between the pre-treated Glibenclamide and Delt-E alone groups as seen in Table 2.

Discussion: These studies demonstrated that Delt-E administration without accompanying fluid resuscitation immediately after severe hemorrhage resulted in ischemic protection, which included improvement in hemodynamic stability markers including increased MAP, decreased HR, increased pulse pressure (i.e. difference between systolic and diastolic pressure), decreased plasma lactate production, and increased survival time. The effects of specific opioid receptor sites activated by Delt-E were assessed by the response of Naltrexone (a universal opioid receptor inhibitor) and BNTX (a delta$_1$ specific opioid inhibitor) and NTB (a delta$_2$ specific opioid receptor inhibitor) on hemodynamic markers in severely hemorrhaged rats. The role of $K_{ATP}$ channel activation was determined by the use of the non-specific $K_{ATP}$ channel blocker, Glibenclamide.

Post-hemorrhage treated controls (1 mL/100 g i.v. saline) exhibited maximum MAP (i.e., 35±9 mmHg), maximum HR (i.e., 425±94 bpm), lactic acid concentration of 8.9±0.12 mmol/L, and pulse pressure of 38.3±0.44 mmHg. In contrast, post-hemorrhage 5.5 mg/kg Delt-E treated rates exhibited maximum MAP (58±7 mmHg) and maximum HR (396±40 bpm), lactic acid (6.5±1.2 mmol/L) and pulse pressure (47.9±0.55 mmHg). At the 5.5 mg/kg dose Delt-E treated animals lived at least six times longer (331 minutes) versus the saline control animals (50 minutes), P<0.01 significance. Using logistic analysis of MAP-HR gain suggests Delt-E$_{var}$ did not significantly alter the baroreflex sensitivity. However, Delt-E facilitates a cardioprotective effect post-hemorrhage through alternate pathways involving lactic acid reduction. A dose response correlation between lactic acid concentration and increased survival was found. It is possible that delta$_2$ specific opioid receptor agonists such as Delt-E and Deltorphin-D$_{variant}$ (Delt-D$_{var}$) may induce a hibernation-like state of metabolic depression following severe hemorrhage, thereby, retarding the anaerobic glycolytic pathway which is known to be increased resulting in decreased levels of circulating lactate. Delt-E may also facilitate a cardioprotective recompensatory recovery mechanism following hemorrhage which entails Delt-E's pulse pressure. The greater the increase in pulse pressure, the greater the survival. The role of pulse pressure in ischemic stress response has not been fully characterized. However, in humans it is known that exercise-induced stress can alter pules pressure which increase stroke volume and cardiac output leading to greater tissue perfusion. Following injections of Delt-E there was a significant increase in pulse pressure with a dose related response leading to greater tissue perfusion. Delt-E also dose dependently enhanced MAP recovery and length of survival following severe hemorrhage as had been previously demonstrated in rats infused with Delt-D$_{var}$ 24 hr prior to severe (53%) volume controlled hemorrhage (Oeltgen et. al 2006).

To further clarify the cellular mechanisms by which activation of the δ$_2$ opioid receptor by Delt-E produces hemodynamic recovery in rat, we studied the role of G$_{i/o}$ proteins and the $K_{ATP}$ channel in mediating this effect. It has been well documented in several tissue types that the δ-opioid receptor is linked to K$^+$ channels via G proteins (Musser et al. 2004). Wild et al. (1991) demonstrated that activation of the δ-opioid receptor via K$^+$ channels produced a cardioprotective effect and the subtypes of this receptor were linked to different K$^+$ channels. Their results demonstrated that the cardioprotective effect produced by the δ$_1$-opioid receptor agonist DPDPE could be negated by Glibenclamide, indicting that the δ$_1$ receptor subtype was linked to neuronal $K_{ATP}$ channels. However, the cardioprotective effect of Deltorphin II, a δ$_2$ opioid receptor agonist, was not blocked by Glibenclamide, which demonstrates that the δ$_2$ receptor subtype is linked to voltage-gated K$^+$ channels and not to $K_{ATP}$ channels (Wild et al. 1991). Our present results further demonstrated that the cardioprotection provided by Delt-E, a δ agonist, was not blocked by Glibenclamide indicating that the hemodynamic recovery protection is mediated by a mechanism not involving $K_{ATP}$ channels, but perhaps by a voltage-gated K$^+$ channel.

The universal antagonist Naltrexone partially blocked the hemodynamic recovery effects of Delt-E indicating that Delt-E was acting upon a δ opioid receptor. Further investigation with specific delta opioid receptor agonists (NTB (δ$_2$) and BNTX (δ$_1$) revealed that only the δ$_2$ opioid receptor agonists NTB blocked Delt-E's effect on shock and survival following severe hemorrhage. Therefore, the site of action for Delt-E is a δ$_2$ opioid receptor which, following intravenous administration, promotes significant recovery of hemodynamic biomarkers after severe hemorrhage.

The studies described herein indicate that Delt-E administration after the occurrence of an event creating a risk of circulatory and hypovolemic shock is an effective treatment. The treatment provides protection against hemorrhage and facilitates recovery.

Study Design: Prehemorrhage Delt-E Infusion

The hemorrhagic shock model used was a volume-controlled model similar to that of Summers et al. *Acad Emerg Med.* 10:587-93 (2003). Twenty male Sprague-Dawley rats (about 325-400 grams) were acclimated to a laboratory environment for a week, and then randomly assigned to one of two groups, controls (n=14) and Delt-E treated group (n=5). Indwelling Teflon 30 catheters were placed in the femoral artery, the femoral vein, and the tail artery of anesthetized rats. The three catheters were combined and exited supraspcapsularly. Rats were then placed in a cage having a plastic cover with a narrow longitudinal slot, which would allow unrestricted movement to food and water, and allow unrestricted access to all three catheters. The femoral artery catheter was used for volume-controlled hemorrhage, the femoral vein catheter was used for delta opioid infusion, and the tail artery catheter was used for blood pressure and heart rate measurements.

Treatment: Twenty-four hours after catheter placement, test rats (n=5) were infused in the femoral vein with about 5.0 mg/kg Delt-E (Tyr-D-Ala-Phe-Ala-Ile-Gly-Asp-Phe-Ser-Ile-$NH_2$; SEQ ID NO: 1) dissolved in 1.0 ml Lactated Ringers (LR) solution pH 7.4. Control rats (n=14) were infused with 1.0 ml Lactated Ringers solution pH 7.4. 24 hours after Delt-E or LR infusion rats were bled at a rate of 3.18 ml/100 grams over a 20-25 min period representing 53% blood loss. Plasma lactate levels were determined at the beginning of hemorrhage (BOH) and end of hemorrhage (EOH) utilizing a Vitros® 950 Chemistry Analyzer (Ortho-Clinical Diagnostics, Rochester, N.Y.). Heart Rate (HR) and blood pressure (BP) were monitored from baseline (just prior to hemorrhage), at the EOH, and through 4 hrs at 30 min intervals. Four hour survival rates for control and test animals were also monitored. Lactate levels represent the BOH and EOH. HR and BP represent all animals at baseline levels, and at the end of hemorrhage and that of survivors at each 30 min time point up to 4 hr. Death was defined as apnea and systolic BP<30 mmHg without pulsations. Surviving animals at the 4.0 hr time point were euthanatized using I.V. sodium pentobarbital 150 mg/kg.

Data Analysis: Hemodynamic values for mean arterial pressure (MAP) and HR were recorded at baseline (immediately prior to hemorrhage) and immediately post-hemorrhage, and for each 30 min time period within the 4 hours of the experiment following hemorrhage. HR, MAP, and lactate data were compared using two groups (Delt-E and control) repeated measures (first two time periods, BOH and EOH) analysis of variance (ANOVA) to determine if there were any group differences. No further inferential statistics were deemed appropriate because of the attrition rate of control subjects in the immediate post hemorrhage period. Subsequent to repeated measures analysis of variance, simple effects for MAP and lactate were analyzed separately for pretest data and post test data using one way analysis of variance. Kaplan-Meir survival analysis was performed to determine the differential effectiveness of Delt-E to survival using death as the criterion. All other cases were treated as censored (animals still living post-experimental period).

Figure 7:
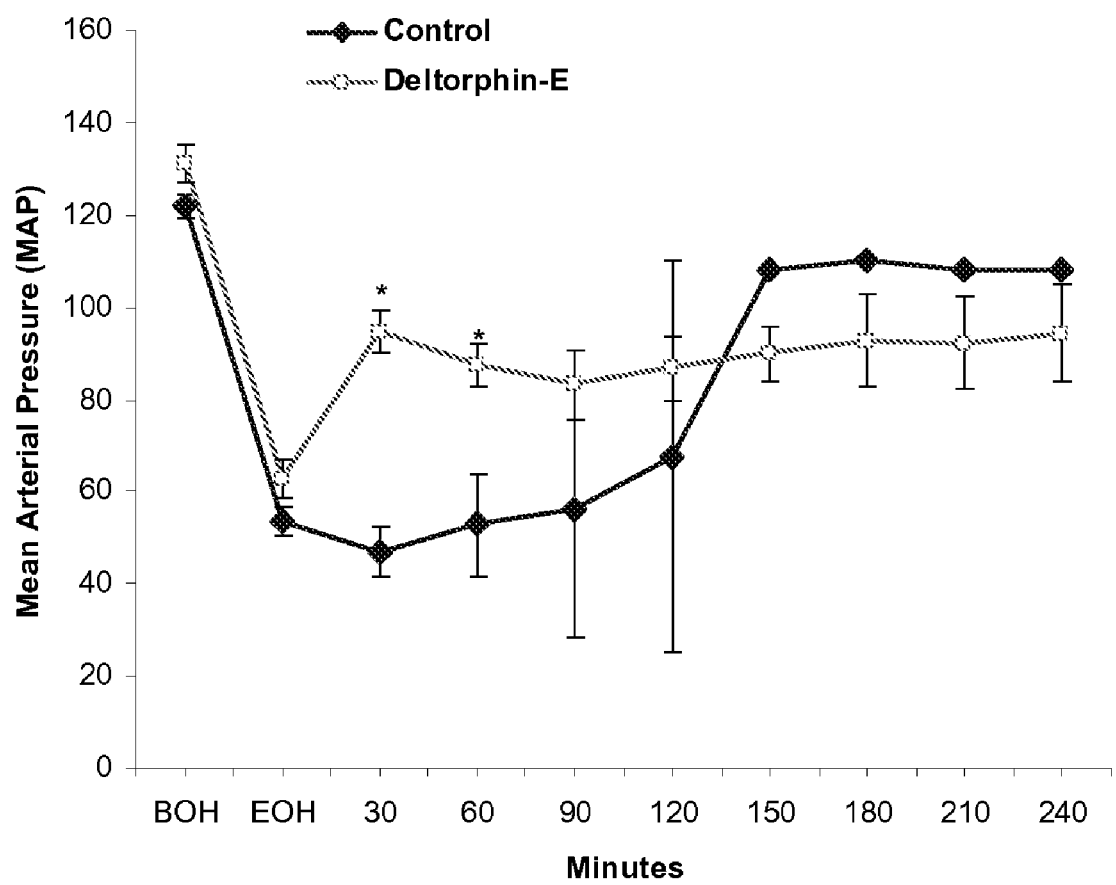
FIG. 7 is a graph comparing mean arterial pressure (MAP, mmHg) as a function of time for Delt-E-treated and control groups where treatment was prior to hemorrhage.

Results: With reference to FIG. 7, twenty-four hours after opioid infusion, mean arterial pressure (MAP) at the beginning of hemorrhage (BOH) trended higher (p=0.06) for the Delt-E treated group (131±4.06 mmHg) vs the control group (122.±2.14 mmHg). MAP for the Delt-E group also trended higher (p=0.06) vs the control group at the end of hemorrhage (EOH) (67.3±3.4 mmHg vs 53.5±2.9 mmHg). MAP of Delt-E treated group was significantly elevated at 30 min posthemorrhage 94.6±4.7 mmgHg vs control 46.9±5.5 mgHg (p=0.005) and at 60 min 87.4±4.5 mmHg vs control 52.8±10.9 mmHg (p=0.015).

Figure 8:
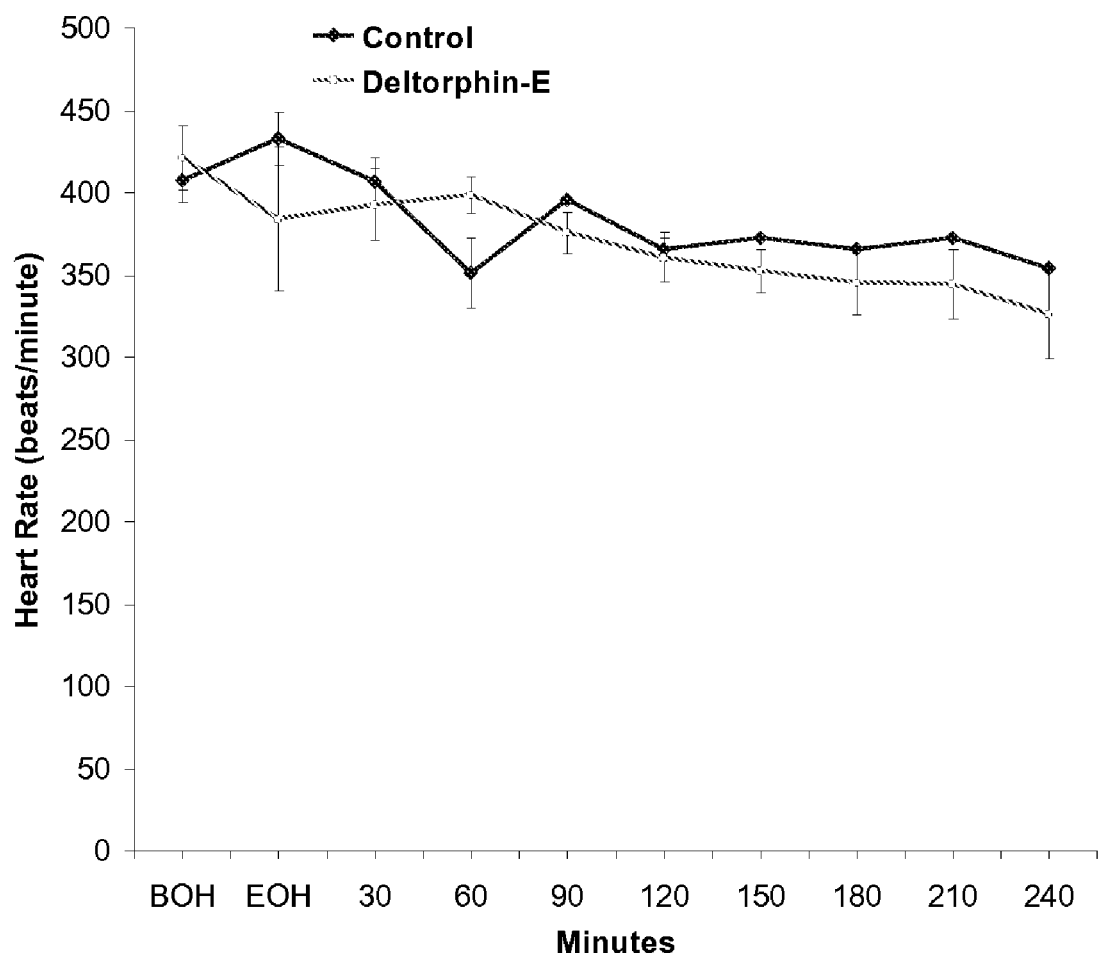
FIG. 8 is a graph comparing average heart rates (HR, beats/minute) as a function of time for Delt-E-treated and control groups, where treatment was prior to hemorrhage.

With reference to FIG. 8, average HR trended downward for both Delt-E and control groups. No significant differences in HR between controls and Delt-E were noted.

Figure 9:
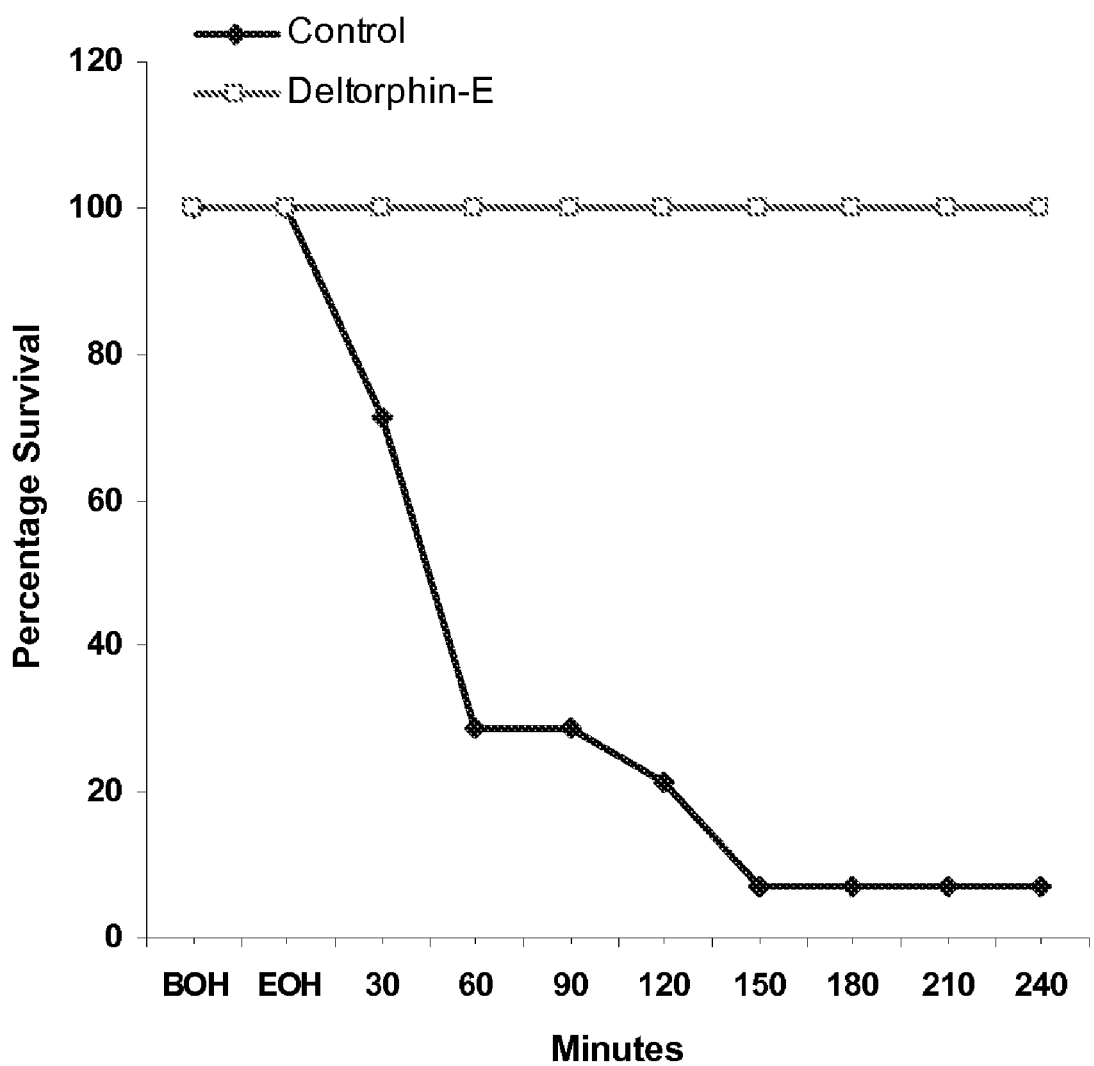
FIG. 9 is a graph comparing the percentage of survivors for Delt-E-treated and control groups as a function of time, where treatment was prior to hemorrhage.

Kaplan-Meier survival analysis revealed a significant difference in survival distributions for the Delt-E vs control group. The chi-square test values and p-levels of the three indices were 16.6, p<0.0000 for the log rank method; 13.1, p=0.0003 for the Breslow method; and 14.7, p=0.0001 for the Tarone-Ware method. FIG. 9 displays the survival summary for both dead and censored subjects in each group for each post-hemorrhage time period, beginning at 30 min. The one-hour survival percentage for controls was 28.6% (4 out of 14) and 100% (5 out of 5) for the Delt-E treated group. The 4 hr survival percentage for controls was 7.1% (1 out of 14) and 100% (5 out of 5) for Delt-E treated group. While only one of the control rats survived past 150 minutes, 100% of the Deltorphin-E treated rats were still alive at the end of the experiment.

Figure 10:
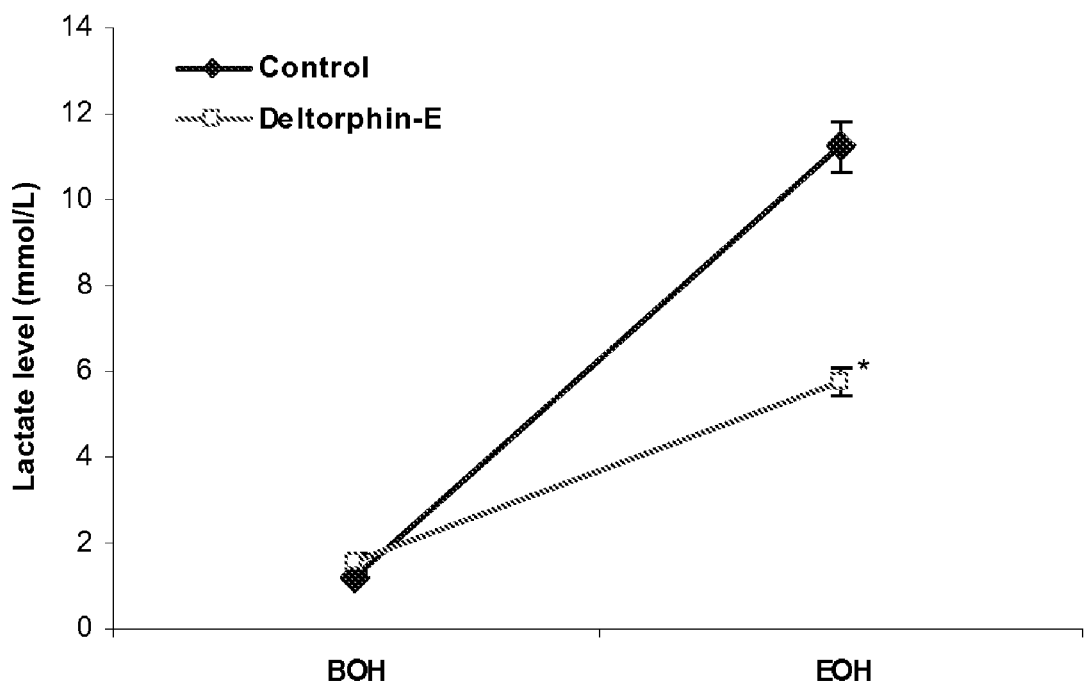
FIG. 10 is a graph comparing lactate levels (mmol/L) in arterial blood samples at the beginning of hemorrhage and at the end of hemorrhage for Delt-E-treated and control groups where treatment was prior to hemorrhage.

With reference to FIG. 10, mean lactic acid levels at the beginning of hemorrhage (BOH) in the control and Delt-E-treated group were not significantly different (1.2±0.4 mmol/l vs 1.54±0.2 mmol/l respectively); however, mean lactic acid levels at end of hemorrhage (EOH) for controls increased nine fold to 11.2±0.6 mmol/l and four-fold for Delt-E treated animals to 5.8±0.3 mmol/l. The Delt-E treated group had a significantly lower lactic acid level (p=0.0004) than the control.

Discussion: These studies demonstrated that Delt-E administration prior to severe hemorrhage resulted in delayed or pharmacological ischemic protection, which improved hemodynamic stability, increased MAP, decreased plasma lactate levels, and enhanced survival rates of tested animals. The rats treated with Delt-E prior to hemorrhage had survival rates of 100% where no concomitant fluid resuscitation was used, compared to survival rates of only 7.1% in control rats that were not pretreated with Delt-E The surviving rats in the Delt-E treated group had MAP of 87.8±5.8 mmHg 4 hr following hemorrhage. A blood pressure of 80 to 90 mmHg is generally sufficient to maintain vital organ perfusion.

Delt-E enhanced the recovery of MAP during the recompensatory phase of hemorrhage. Although, lactic acid levels were almost identical for controls (1.2±0.4 mmol/l) and Delt-E-treated animals (1.3±0.1 mol/l) at the beginning of hemorrhage, lactate levels were significantly lower for the Delt-E-treated group (5.8±0.3 mmol/l) at the end of hemorrhage than for controls (11.2±0.6 mmol/l). Without wishing to be bound by theory, such findings indicate that Delt-E pretreatment may have retarded the anaerobic glycolytic pathway leading to the production of lactate and raised the interesting possibility that this opioid-mediated ischemic protection may involve induced metabolic depression similar to that seen in hibernation.

Without wishing to be bound by theory, such findings indicate that Delt-E can provide ischemic protection during the recompensatory phase of hemorrhage by acting as hibernation-like metabolic inhibitors. Delt-E treatment without concomitant fluid resuscitation can facilitate improved survival during hemorrhagic shock. It is now being recognized that type and time of resuscitation fluid used may actually potentiate cellular injury caused by hemorrhagic shock leading to the concept of "resuscitation injury." Thus the use of Delt-E treatment can circumvent some or all of the problems associated with the use of the current resuscitation fluids. Since large fluid volumes would not be required when administering Delt-E, it could be especially useful in a civilian or military trauma setting, where Delt-E could be rapidly administered by first responders during the initial hour following trauma, when lifesaving intervention is most critical. The use of Delt-E may also have clinical applicability as a pharmacological ischemic preconditioning agent where ischemic events can be anticipated such as occur in off-bypass cardiac surgery, percutaneous transluminal coronary angioplasty, or stenting procedures. Delt-E treatment is useful in providing ischemic protection in clinical scenarios of planned ischemia, as well as in treating hemorrhagic shock.

Throughout this application, various publications are referenced. All such references are incorporated herein by reference, including those in the following list:

U.S. Pat. No. 6,900,178 to Oeltgen, et al. PROTECTION AGAINST ISCHEMIA AND REPERFUSION INJURY U.S. Pat. No. 6,875,742 to Oeltgen, et al. METHOD FOR TREATING CYTOKINE MEDIATED HEPATIC INJURY U.S. Pat. No. 6,544,950 to Oeltgen, et al. SEVENTEEN AMINO ACID PEPTIDE (PEPTIDE P) FOR TREATING ISCHEMIA AND REPERFUSION INJURY U.S. Pat. No. 6,380,164 to Oeltgen, et al. METHOD FOR TREATING CYTOKINE MEDIATED HEPATIC INJURY U.S. Pat. No. 6,316,411 to Oeltgen, et al. PROTECTION AGAINST ISCHEMIA AND REPERFUSION INJURY U.S. Pat. No. 6,294,519 to Oeltgen, et al. METHOD FOR TREATING ISCHEMIA U.S. patent application Ser. No. 11/618,129 to Oeltgen, et al. METHOD FOR TREATING CIRCULATORY AND HYPOVOLEMIC SHOCK Ayala, A., Wang, P., Baz, F., Perrin, M. M., Ertel, W., Chaudry, I. H. Differential alterations in plasma IL-6 and TNF levels following trauma and hemorrhage. *Am J Physiol* 260: R167-71, 1991.

Balogh, Z., McKinely, B. A., Cocanour, C. S. Supranormal trauma resuscitation causes more cases of abdominal syndrome. *Archives of Surgery* 138:637-642, 2003.

Bell, S. P., Sac, M. N., Patel, A., Opie, L. H., Yellon, D. M. δ-Opioid receptor stimulation mimics ischemic preconditioning in human heart muscle. *J Am Coll Cardiol.* 36:2296-02, 2000.

Bernard, C., Alain, M., Simone, C., Xavier, M., Jean-Fracois, M. Hydroxyethyl starch and osmotic nephrosis-like lesions in kidney transplants. Lancet. 348:1595, 1996.

Bicknell, W. H., Matthew, J., Wall, M. J. Jr., Pepe, P. E., Martin, R. R., Ginger, V. F., Allen, M. K., Mattox, K. L.: Immediate versus delayed fluid resuscitation for hypotensive patients with penetrating torso injuries. *N Engl J Med* 331:1105-1109, 1994.

Bolling, S. F., Schwartz, C. F., Oeltgen, P. R., Kilgore, K., Su, T-P. Opiods confer myocardial tolerant to ischemia: Interaction of delta opioids agonists and antagonists. *J Thorac Caradiovasc Surg.* 122: 476-81, 2001.

Chien, S., Oeltgen, P. R., Diana, J. M., Salley, R., Su, T-P. Extension of tissue survival time in multiorgan block preparation using delta opioid DADLE. *J. Thorac Cardiovasc Surg,* 107: 964-67, 1994.

Cittanova, M. L., Leblanc, I., Legendre, C. et. al. Effect of hydroxyethyl starch in brain-dead kidney donors on renal function in kidney transplant recipients. *Lancet* 348:1620-1622, 1996.

Coimbra, R., Hoyt, D. B., Junger, W. G., et. al. Hypertonic saline resuscitation decreases susceptibility to sepsis after hemorrhagic shock. *J Trauma* 42:602-07, 1997.

Doyle, J. A., Davis, D. P., Hoyt, D. B. The use of hypertonic saline in the treatment of traumatic brain injury. *J Trauma* 50:367-83, 2000.

Evan, R. G., Ventura, S., Dampney, R. A., Ludbrock, J. Neural mechanisms in cardiovascular responses to acute central hypovolemia. *Clin Exp. Pharmacol Physiol* 28:479-87, 2001.

Flynn, F. W., Stricker, M. Hypovolemia stimulates intraoral intake of water and NaCl solution in intact rats but not in chronic decerebrate rats. *Physiol Behav* 80:281-287, 2003.

Fryer, R. M., Hsu, A., Eels, J. T., Nagase, H., Gross, G. J. Opioid-Induce Second Window of Cardioprotection—potential role of mitochondrial KATP channels, *Circ Res.* 84: 846-51, 1999.

Fryer, R. M., Wang, Y., Hsu, A. K., Gross, G. J. Essential activation of PKC-δ in opioid-initiated cardioprotection. *Am J Physiol Heart Cir Physiol.* 280:H1346-53, 2001.

Gan, T. J., Bennett-Guerro, E., Phillips-Bute, B. et. al. Hextend®, a physiologically balanced plasma expander for large volume use in major surgery: a randomized phase III clinical trail. *Anesthesiology Analgesia* 88:992-998, 1999.

Govindaswami, M., Bishop, P. D., Kindy, M. S., Oeltgen, P. R.: Neuroprotective effects of opioid-like hibernation factors in cerebral ischemia. *FASEB J* 17(5) A895, No 579.10 (2003)

Govindaswami, M., Rodgers, J. R., Lesnaw, J., Oeltgen, P. R. A cell culture assay for delta opioids and opioid-like hibernation specific factors (HSF). *FASEB J.* 16:(5)A852, No 643.25, 2003.

Govindaswami, M., Sanchez, A., Bishop, P. D., Bruce, D. S., Oeltgen, P. R. Opioid-like hibernation factors provide protection to ischemic myocardium. In Heldmaier G, Kingenspor M (eds: *Life in the Cold:* 11*th International Symposium.* Berlin, Germany: Springer-Verlag Publishers, pp 377-384, 2000.

Greaves, I., Porter, K. M., Ryan, J. M., eds. *Shock.* In Trauma Care Manual. London: Arnold; 78-79, 2000.

Head, G. A., McCarty, R. Vagal and sympathetic components of the heart rate range and gain of the baroreceptors-heart rate reflex in conscious rats. *J Auton Nerv Syst* 21:203-213, 1987.

Huraux, C., Ankri, A. A., Eyraud, D. et. al. Hemostatic changes in patients receiving hydroxyethyl starch: the influence of ABO blood group. *Anesth Analg.* 92:1396-1401, 2001.

Husted, T. L., Lentch, A. B., Govindaswami, M., Oeltgen, P. R., Rudich, S. M. A delta-2 opioid agonist inhibits p38 MAPK and suppresses activation of murine macrophages. *J. Surg Research* 28:45-49, 2005.

Jonville-Bera, A. P., Autret-Leca, E., Gruel, Y. Acquired type I von Willebrand's disease associated with highly substituted hydroxyethyl starch. *N Engl J Med.* 345:622-623, 2001.

Kark, M., Tanaka, S., Bolling, S. F., Su, T-P, Oeltgen, P. R., Haverich, A. Myocardial protection by ischemic preconditioning and δ opioid receptor activation in the isolated working rat heart: *J Thorac Cardiovasc. Surg.* 122: 986-92, 2001.

Kevelaitis, E., Peynet, J., Mousa, C., Launay, J. M., Menaschep. Opening of potassium channels: the common cardioprotective link between preconditioning and natural hibernation? *Circ.* 99:3079-85, 1999.

Koustova, E., Stanton, K., Gushchin, V., et. al. Effects of lactated Ringer's solution on human leukocytes. *J. Trauma* 52: 872-878, 2002

Kowalenko, T., Stern, S., Dronen, S., Wang, X: Improved outcome with hypotensive resuscitation of uncontrolled hemorrhage shock in a swine model. *J Trauma* 33:349-353, 1992.

Krauz, M. M., Horn, Y., Gross, D. The combined effect of small volume hypertonic saline and normal saline solutions in uncontrolled hemorrhagic shock. *Surg Gyn Obs.* 174:363-68, 1992.

Kumle, B., Boldt, J., Piper, S., Schmidt, C., Suttner, S., Salopek, S. The influence on different intravascular volume replacement regimens on renal function in the elderly. *Anesth Analg.* 89:1124-1130, 1999.

Ley, K. Plugging the leaks. *National Medicine* 7:1105-1106, 2001.

Liang, B. T., Gross, G. J. Direct preconditioning of cardiac myocytes via opioid receptors and KATP channels: *Circ Res.* 84: 1396-00, 1999.

Lucas, C. E. The water of life: a century of confusion. *J. American College of Surgeons* 192: 86-93, 2001.

Marastoni, M., Tomatis, R., Balboni, G., Salvadori, S., Lazarus, L. H. On the degradation of deltorphin peptides by plasma and brain homogenates. *Farmaco* 46:1273-1279, 1991

Mattox, K. L., Maningas, P. A., Moore, E. E. et. al. Prehospital hypertonic saline/dextran infusion for post-traumatic hypotension. *Ann Surg;* 213:482-91, 1991.

Mayfield, K. P., D'Alecy, L. G. Delta-I opioid agonist acutely increases hypoxic tolerance. *J Pharmacol Exp Ther.* 268: 683-88 (1994).

Mazzoni, M. C., Borgstrom, P., Intaglietta, M., et. al. Lumenal narrowing and endothelial cell swelling in skeletal muscle capillaries during hemorrhagic shock. *Circ. Shock* 29:27-30, 1989.

McBride, S. M., Smith-Sonneborn, J., Oeltgen, P., and Flynn, F. W. opioid receptor agonist facilitates mean arterial pressure recovery after hemorrhage in conscious rats. *Shock* 23(3) 264-268, 2005.

Moore, E. E., Hypertonic saline dextran for post-injury resuscitation: Experimental background and clinical experience. *Aust N Z F Surg;* 61732-36, 1991.

Moore, F. A., McKinley, B. A., Moore, E. E. Trauma III The next generation in shock resuscitation. Lancet 363: 1988-1996, 2004.

Musser, J. B., Bentley, T. B., Griffith, S., Sharma, P, Karaian, J., Mongan, P. Hemorrhagic shock in swine:nitric oxide and potassium sensitive adenosine triphosphate channel activation. *Anesthesiology* 101:399-408, 2004.

Nilekani, S. P., Oeltgen, P. R., DiMartino, D., Turker, M. In vitro analysis of biologically active factors in winter-hibernating and summer-active woodchuck plasma. *FASEBJ.* 4(4); 854 (1990).

Noga, M., Hayashi, T. The ubiquitin gene expression following transient forebrain ischemia. *Molecular Brain Res.* 6:261-67, 1996.

Oeltgen P. R., Govindaswami M., Witzke D. B. 24-hour pretreatment with delta opioid enhances survival from hemorrhagic shock. *Acad Emerg Med.* 13(2):127-33, 2006.

Oeltgen, P. R., Nilekani, S., Nuchols, P., Spurrier, W. A., Su T-P. Further studies on opioids and hibernation: Delta opioid receptor ligand selectively induced hibernation in summer-active ground squirrels. *Life Sciences* 43:1565-74, 1988.

Omar, M. N., Shouk, T. A., Khaleq, M. A. Activity of blood coagulation and fibrinolysis during and after hydroxyethyl starch (HES) colloidal volume replacement. *Clin Biochem.* 32:269-274, 1999.

Owens, T. M., Watson, W. C., Prough, D. S., Uschida, T., Kramer, G. C. Limiting initial resuscitation of uncontrolled hemorrhage reduces internal bleeding and subsequent volume requirements. J Trauma 39:200-207, 1995.

Patel, H. H., Hsu, A. K., Peart, J. N., Gross, G. J. Sarcolemmal KATP channel triggers opioid-induced delayed cardioprotection: *Circ Research* 91: 186-188, 2002

Patel, H. H., Hsu, A. K., Peart, J. N., Gross, G. J. Sarcolemmal KATP channel triggers opioid-induced delayed cardioprotection. *Circ Res.* 91:186-89, 2002.

Pope, A., French, G., Longnecker, D. E., for the Committee on Fluid Resuscitation for Combat Casualties: *Fluid Resuscitation.* Washington, D.C.: National Academy Press, 1999.

Raffle, A. D., Rath, P. A., Michell, M. W., Kirschner, R. A., Deyo, D. J., Prough, D. S., Grady, J. J., Kramer, G. C. Hypotensive resuscitation of multiple hemorrhages using crystalloid and colloids. *Shock* 22(3) 262-269, 2004.

Rezende-Neto, J. B., Moore, E. E., Masuno, T. The abdominal compartment syndrome as a second insult during systemic neutrophil priming provokes multiple organ injury. Shock 20, 303-308, 2003.

Rhee, P., Wang, D., Ruff, P., et. al. Human neutrophil activation and increased adhesion by various resuscitation fluids. *Crit Care Medicine* 28:74-75, 2000

Saeed, R. W., Stefano, G. B., Murga, J. D., Short, T. W., QiF, Bilfinger, T. V., Magazine, H. I. Expression of functional delta opioid receptors in vascular smooth muscle. *International J Molec Med.* 6:673-77, 2000

Schortgen, F., Lacerade, J. C., Bruneel, F. et. al. Effects of hydroxyethyl starch and gelatin on renal function in severe sepsis: a multicenter randomized study. *Lancet,* 357:911-916, 2001.

Schortgen, P., Lacherade, J. C., Bruneel, F. et. al. Effects of hydroxyethylstarch and gelatin on renal function in severe sepsis: a multicentre randomized study. *Lancet.* 357:911-916, 2001.

Schultz, J. E., Hsu, A. K., Gross, G. J. Morphine mimics the cardioprotection effect of ischemic preconditioning via glibenclamide-sensitive mechanism in the rat heart. *Cir Res* 78:1100-04, 1996.

Schultz, J. E, Hsu, A. K., Gross, G. J. Ischemic preconditioning and morphine-induced cardioprotection involve the delta-opioid receptor in the intact rat heart. *J Mol Cell Cardio.* 29:2187-95, (1997)

Schultz, J., Hsu, A., Nasase, H., Gross, G. J. TAN-67, a 81-opioid receptor agonist reduces infarct size via activation of G i/o proteins and KATP channels. *Am J Physiol.* 274: H909-14, 1998.

Schultz, J. E., Rose, E., Yao, Z., Gross, G. J. Evidence for involvement of opioid receptors in ischemic preconditioning in rat hearts. *Am J Physiol.* 268 (H2) 157-162, 1995.

Shackford, S. R. Effects of small-volume resuscitation on intracranial pressure and related cerebral variables. *J Trauma* 42:S48-S53, 1997.

Sharma, H. A. S., Maulik, N., Cho, B. C., Das, D. K., Verdouw, P. D. Coordinated expression of heme oxygenase-1 and ubiquitin in the porcine heart subjected to ischemia and reperfusion. *Mol Cell Biochem.* 157:111-16, 1996.

Shenkar, R., Coulson, W. F., Abraham, E. Hemorrhage and resuscitation induce alterations in cytokine expression and the development of acute lung injury, *Am J Respir Cell Mol Biol.* 10:290-97, 1993.

Sigg, D. C., Coles, J. A., Oeltgen, P. R., Iaizzo, P. A. Role of delta-opioid receptor agonists on infarct size reduction in swine. *Am J Physiol Heart Circ Physiol.* 282 (H1) 953-60, 2002.

Simma, B., Burger, R., Falk, M, et. al. A prospective, randomized, and controlled study of fluid management in children with severe head injury: lactated Ringer's solution versus hypertonic saline. *Crit Care Med.* 26:1265-70, 1998.

Smith, G. J., Kramer, G. C., Perron, P. A comparison of several hypertonic solutions of resuscitation of bled sheep. *J Surg Res.* 39:517-28, 1985.

Smith-Sonneborn, J., Gottsch, H., Cubin, E., Oeltgen, P. R., Thomas, P. Alternative strategy for stress tolerance: *Opioids J. Gerontol: Biolog Sci.* 59A:433-40, 2004.

Stefano, G. B., Salzet, M., Hughes, T. K., Bilfinger, T. V. 82 opioid receptor subtype on human vascular endothelium uncouples morphine stimulated nitric oxide release. *International J Cardiol.* 64:S43-51, 1998

Stern, S. A., Dronen, S. C., Birrer, P., Wang, X. Effect of blood pressure on hemorrhage volume and survival in a near-fatal hemorrhage model incorporating a vascular injury. *Ann Emerg Med* 22:155-163, 1993.

Stern, S. A., Dronen, S. C. Wang, A: Multiple resuscitation regimens in a near-fatal procine aortic injury hemorrhage model. Acad Emerg Med 2:89-97, 1995

Stoll, M., Trieb, J., Shenk, J. F., et. al. No coagulation disorders under high dose volume therapy with low molecular weight hydroxyethyl starch. Hemostasis 27:251-258, 1997.

Summers, R. L., Zizhuang, L., Hildebrandt, D.: Effect of a 8 receptor agonist on duration of survival during hemorrhagic shock. *Acad Emerg Med.* 10:587-93, 2003.

Tabuchi, N., de Hann, J., Gallandat Huet, R. C., Boonstra, P. W, van Oeveren, W. Gelatin use impairs platelet adhesion during cardiac surgery. *Thromb Haemos.* 74:1447-1451, 1995.

Tremblay, L. N. Rizoli, S. B., Brennemen, F. D. Advances in fluid resuscitation of hemorrhagic shock. *Canadian J. Surgery* 44⊛3) 172-179, 2001.

Treib, J., Haass, A., Pindur, G., et. al. Increased hemorrhagic risk after repeated infusion of highly substituted medium molecular weight hydroxyethyl starch. *Arzneimittelforschung.* 47:18-22, 1997.

Vamvalas, E. C., Blakchman, M. A. Prestorage versus post storage white cell reduction for the prevention of the deleterious immunomodulatory effects of allogenic blood transfusions. *Transfusion Med. Rev.* 14:23-33, 2000.

van Breukelen, F., Carey, V. Ubiquitin conjugate dynamics in the gut and liver of hibernating ground squirrels. *J Comp Physiol.* 172:269-73, 2002

Vassar, M. J., Perry, C. A., Holcroft, J. W. Analysis of potential risks associated with 7.5% sodium chloride resuscitation of traumatic shock. *Arch Surg.* 125:1309-15, 1990.

Velasco, I. T., Pontieri, V., Rocha-e-Silva, M., et. al. Hyperosmotic NaCl and severe hemorrhagic shock. *Amer J. Physiol* 239: H664, 1980.

Videm, V., Fosse, E., Svennevig, J. L., Platelet preservation during coronary bypass surgery with bubble and membrane oxygenators: effect of albumin priming *Perfusion.* 8:409-415, 1993.

Voelckel, W. G., Lindner, K. H., Wenzel, V., Bonatti, J., Hangler, H., Frimmel, C., Kuhnszberg, E., Lingnau, W. Effects of vasopressin and epinephrine on splanchnic blood flow and renal function during and after cardiopulmonary resuscitation in pigs: *Crit Care Med* 28:1083-88, 2000.

Voelckel, W. G., Lurie, K. G., Lindner, K. H., Zielinski, T., McKnite, S., Krismer, A. C., Wenzel, V. Vasopressin improves survival after cardiac arrest in hypovolemic shock: *Anesth Analg* 91:627-34, 2000.

Wade, C. E., Kramer, G. C., Grady, J. J., et. al. Efficacy of hypertonic 7.5% saline and 6% dextran-70 in treating trauma: a meta-analysis of controlled clinical studies. *Surgery* 122:609-16, 1997.

Wenzel, V., Lindner, K. H. Employing vasopressin during cardiopulmonary resuscitation and vasodilatory shock as a lifesaving vasopressor: *Cardiovasc Res* 51:529-41, 2001.

Wild, K. D., T. Vanderah, H. I. Mosberg, and F. Porreca: Opioid d receptor subtypes are associated with different potassium channels. *Eur. J. Pharmacol.* 193: 135-136, 1991.

Yellon, D. M., Baxter, G. A. "second window of protection" or delayed preconditioning phenomenon: future horizons for myocardial protection. *J Mol Cell Cardiol.* 27:1023-34, 1995.

Zallen, G., Moore, E. E., Tamura, D. Y., et. al. Hypertonic saline resuscitation abrogates neutrophil priming by mesenteric lymph. *J Trauma* 48:45-48, 2000.

Zhang, J., Haddad, Xia, Y. Delta-, but not mu- and kappa-opioid receptor activation protects neocortical neurons from glutamate-induced excitotoxic injury. *Brain Res.* 885: 143-53 (2000).

---

What is claimed is:

1. A pharmaceutical composition for treating shock, comprising:
   a pharmaceutically effective amount of an isolated Deltorphin-E polypeptide, comprising:
   (a) a polypeptide comprising the sequence as set forth in SEQ ID NO: 1; or
   (b) a polypeptide encoded by a nucleic acid comprising the nucleic acid sequence as set forth in SEQ ID NO: 2, wherein the C-terminus of the polypeptide is modified with $NH_2$; and
   a pharmaceutically acceptable carrier.

2. The pharmaceutical composition for treating shock of claim 1, comprising:
   a pharmaceutically effective amount of an isolated Deltorphin-E polypeptide comprising the sequence as set forth in SEQ ID NO: 1; and
   a pharmaceutically acceptable carrier.

3. An isolated Deltorphin-E polypeptide, comprising:
   (a) a polypeptide comprising the sequence as set forth in SEQ ID NO: 1; or
   (b) a polypeptide encoded by a nucleic acid comprising the nucleic acid sequence as set forth in SEQ ID NO: 2, wherein the C-terminus of the polypeptide is modified with $NH_2$.

4. The isolated Deltorphin-E polypeptide of claim 3, comprising the sequence as set forth in SEQ ID NO: 1.

5. A method of treating shock in a subject, comprising administering an effective amount of the polypeptide of claim 3.

6. The method of claim 5, wherein the polypeptide is administered concurrently with or before onset of shock.

7. The method of claim 5, wherein the polypeptide is administered concurrently with or before onset of an event that creates a risk of shock.

8. The method of claim 7, wherein the polypeptide is administered up to about 24 hours before onset of the event.

9. The method of claim 7, wherein the event is hemorrhage.

10. The method of claim 7, wherein the event is a planned surgery.

11. The method of claim 10, wherein the planned surgery is selected from: heart valve replacement surgery, coronary artery bypass graft surgery, stint placement surgery, orthopedic surgery, organ repair surgery, organ transplantation surgery, and a surgery to implant a device.

12. The method of claim 5, wherein the polypeptide is administered subsequent to onset of shock.

13. The method of claim 12, wherein the polypeptide is administered up to about 4 hours subsequent to onset of shock.

14. The method of claim 5, wherein the polypeptide is administered subsequent to onset of an event that creates a risk of shock.

15. The method of claim 14, wherein the polypeptide is administered up to about 4 hours subsequent to onset of an event that creates a risk of shock.

16. The method of claim 14, wherein the event is hemorrhage.

17. The method of claim 5, wherein the treatment produces at least one desired effect, selected from: a prophylactic effect, and a therapeutic effect.

18. The method of claim 17, wherein the treatment produces a prophylactic effect and a therapeutic effect.

19. The method of claim 17, wherein the treatment produces a prophylactic effect, selected from: reducing the risk of shock, and reducing the risk of injuries resulting from shock.

20. The method of claim 17, wherein the treatment produces a therapeutic effect, selected from: curing or mitigating the shock, and restoring perfusion to organs and tissues.

21. The method of claim 5, wherein the shock is hemorrhagic shock.

22. The method of claim 5, wherein the shock is hypervolemic shock.

23. The method of claim 5, wherein the shock is characterized by a state of whole body ischemia.

* * * * *

SEQUENCE LISTING

```
<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (2)..(2)
<223> OTHER INFORMATION: X=D-Ala
<220> FEATURE:
<221> NAME/KEY: MISC_FEATURE
<222> LOCATION: (10)..(10)
<223> OTHER INFORMATION: X=Ile-NH2

<400> SEQUENCE: 1

Tyr Xaa Phe Ala Ile Gly Asp Phe Ser Xaa
1               5                   10
```

```
<210> SEQ ID NO 2
<211> LENGTH: 30
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (3)..(3)
<223> OTHER INFORMATION: n= T or C
<220> FEATURE:
<221> NAME/KEY: misc_feature
<222> LOCATION: (6)..(6)
<223> OTHER INFORMATION: n= A, G, T, or C
<220> FEATURE:
<221> NAME/KEY: misc_feature
<222> LOCATION: (9)..(9)
<223> OTHER INFORMATION: n= T or C
<220> FEATURE:
<221> NAME/KEY: misc_feature
<222> LOCATION: (12)..(12)
<223> OTHER INFORMATION: n= A, G, T, or C
<220> FEATURE:
<221> NAME/KEY: misc_feature
<222> LOCATION: (15)..(15)
<223> OTHER INFORMATION: n= A, C, or T
<220> FEATURE:
<221> NAME/KEY: misc_feature
<222> LOCATION: (18)..(18)
<223> OTHER INFORMATION: n= A, G, T, or C
<220> FEATURE:
<221> NAME/KEY: misc_feature
<222> LOCATION: (21)..(21)
<223> OTHER INFORMATION: n= T or C
<220> FEATURE:
<221> NAME/KEY: misc_feature
<222> LOCATION: (24)..(24)
<223> OTHER INFORMATION: n= T or C
<220> FEATURE:
<221> NAME/KEY: misc_feature
<222> LOCATION: (27)..(27)
<223> OTHER INFORMATION: n= T or C
<220> FEATURE:
<221> NAME/KEY: misc_feature
<222> LOCATION: (30)..(30)
<223> OTHER INFORMATION: n= T, C, or A

<400> SEQUENCE: 2
tangcnttng cnatnggnga nttnagnatn                                    30
```